United States Patent
Hourtash et al.

(10) Patent No.: US 9,675,421 B2
(45) Date of Patent: *Jun. 13, 2017

(54) SYSTEMS AND METHODS FOR CANCELLATION OF JOINT MOTION USING THE NULL-SPACE

(71) Applicant: Intuitive Surgical Operations, Inc., Sunnyvale, CA (US)

(72) Inventors: Arjang M. Hourtash, Santa Clara, CA (US); Pushkar Hingwe, Fremont, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 48 days.

This patent is subject to a terminal disclaimer.

(21) Appl. No.: 14/802,866

(22) Filed: Jul. 17, 2015

(65) Prior Publication Data

US 2016/0045270 A1    Feb. 18, 2016

Related U.S. Application Data

(63) Continuation of application No. 13/967,606, filed on Aug. 15, 2013, now Pat. No. 9,107,683.

(51) Int. Cl.
- *A61B 19/00* (2006.01)
- *A61B 34/30* (2016.01)

(Continued)

(52) U.S. Cl.
CPC .............. *A61B 34/30* (2016.02); *A61B 34/35* (2016.02); *A61B 34/37* (2016.02); *B25J 9/1643* (2013.01);

(Continued)

(58) Field of Classification Search
CPC ......... A61B 34/30; A61B 34/32; A61B 34/35; A61B 34/37; G05B 2219/40367;

(Continued)

(56) References Cited

U.S. PATENT DOCUMENTS 5,737,500 A * 4/1998 Seraji .................... B25J 9/1643
                                                318/568.11
6,317,651 B1   11/2001 Gerstenberger et al.

(Continued)

FOREIGN PATENT DOCUMENTS

EP     1885273 B1    2/2012
WO  WO-2006124390 A2  11/2006

(Continued)

OTHER PUBLICATIONS

Ex Parte Quayle Action mailed Jan. 28, 2015 for U.S. Appl. No. 13/967,606, filed Aug. 15, 2013, 6 pages.

(Continued)

*Primary Examiner* — Spencer Patton

(74) *Attorney, Agent, or Firm* — Schwegman Lundberg & Woessner, P.A.

(57) ABSTRACT

Devices, systems, and methods are disclosed for cancelling movement of one or more joints of a telesurgical manipulator to effect manipulation movement of an end effector. Methods include calculating movement of joints within a null-perpendicular space to effect desired end effector movement while calculating movement of one or more locked joints within a null-space to cancel the movement of the locked joints within the null-perpendicular-space. Methods may further include calculating movement of one or more joints to effect an auxiliary movement or a reconfiguration movement that may include movement of one or more locked joints. The auxiliary and reconfiguration movements may overlay the manipulation movement of the joints to (Continued)

allow movement of the locked joints to effect the auxiliary movement or reconfiguration movement, while the movement of the locked joints to effect manipulation is canceled. Various configurations for devices and systems utilizing such methods are provided herein.

20 Claims, 22 Drawing Sheets

Related U.S. Application Data

(60) Provisional application No. 61/683,638, filed on Aug. 15, 2012.

(51) Int. Cl.
*A61B 34/37* (2016.01)
*A61B 34/35* (2016.01)
*B25J 9/16* (2006.01)
*A61B 34/32* (2016.01)

(52) U.S. Cl.
CPC ......... *A61B 34/32* (2016.02); *A61B 2034/306* (2016.02); *B25J 9/1607* (2013.01); *G05B 2219/40362* (2013.01); *G05B 2219/40365* (2013.01); *G05B 2219/40367* (2013.01)

(58) Field of Classification Search
CPC ......... G05B 2219/40362; Y10S 901/02; Y10S 901/14; Y10S 901/15; B25J 9/1607; B25J 9/1643; B25J 18/007
See application file for complete search history.

(56) References Cited

U.S. PATENT DOCUMENTS

| | | | |
|---|---|---|---|
| 6,368,332 B1 | 4/2002 | Salcudean et al. | |
| 6,786,896 B1 | 9/2004 | Madhani et al. | |
| 8,004,229 B2 | 8/2011 | Nowlin et al. | |
| 9,107,683 B2 * | 8/2015 | Houtash .............. | A61B 19/22 |
| 9,296,104 B2 | 3/2016 | Swarup et al. | |
| 9,345,544 B2 | 5/2016 | Hourtash et al. | |
| 9,375,284 B2 | 6/2016 | Hourtash | |
| 9,415,510 B2 | 8/2016 | Hourtash et al. | |
| 9,468,501 B2 | 10/2016 | Hourtash et al. | |
| 2013/0325029 A1 | 12/2013 | Hourtash et al. | |
| 2014/0316430 A1 | 10/2014 | Hourtash | |
| 2014/0358161 A1 | 12/2014 | Hourtash et al. | |

FOREIGN PATENT DOCUMENTS

| | | |
|---|---|---|
| WO | WO-2007076119 A2 | 7/2007 |
| WO | WO-2013078529 A1 | 6/2013 |
| WO | WO-2013181503 A1 | 12/2013 |
| WO | WO-2013181507 A1 | 12/2013 |
| WO | WO-2013181516 A1 | 12/2013 |
| WO | WO-2014028703 A1 | 2/2014 |
| WO | WO-2014146095 A1 | 9/2014 |
| WO | WO-2014146107 A1 | 9/2014 |
| WO | WO-2014146113 A1 | 9/2014 |
| WO | WO-2014146119 A1 | 9/2014 |
| WO | WO-2014146120 A1 | 9/2014 |

OTHER PUBLICATIONS

Ginhoux R., et al., "Active Filtering of Physiological Motion in Robotized Surgery Using Predictive Control," IEEE Transactions on Robotics, 2003, 12 pages.
International Search Report and Written Opinion for Application No. PCT/US13/55082, mailed on Nov. 4, 2013, 11 pages.
King H.H., et al., "Preliminary Protocol for Interoperable Telesurgery," IEEE Explore, Downloaded on Dec. 7, 2009, 6 pages.
Nenchev, et al., "Reaction Null-Space Control of Flexible Structure Mounted Manipulator Systems," IEEE Transactions on Robotics and Automation, 1999, vol. 15 (6), pp. 1011-1023.
Notice of Allowance mailed Apr. 13, 2015 for U.S. Appl. No. 13/967,606, filed Aug. 15, 2013, 5 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP13829979.7, mailed on Mar. 15, 2016, 8 pages.

\* cited by examiner

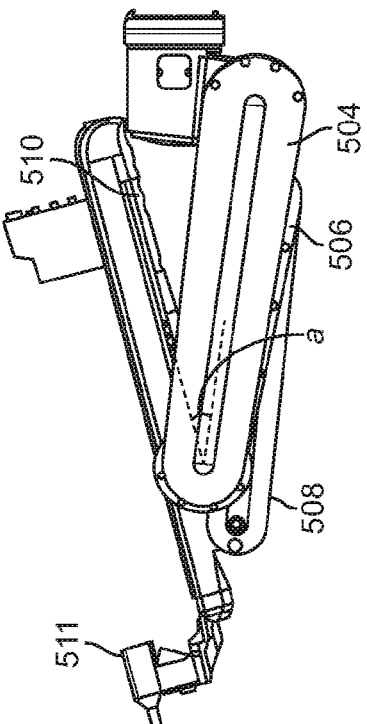
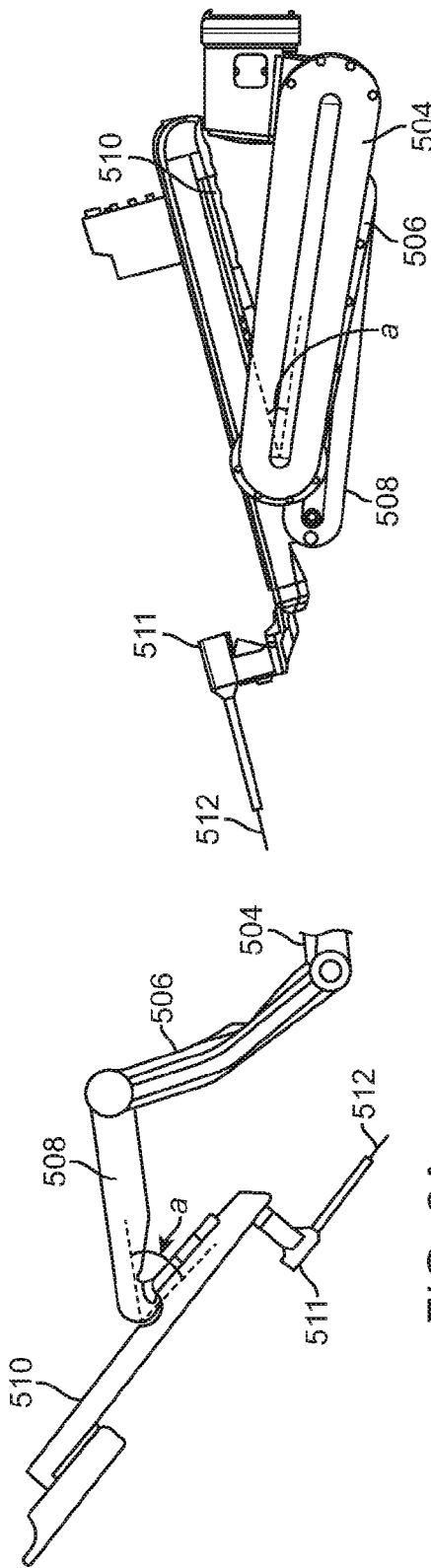
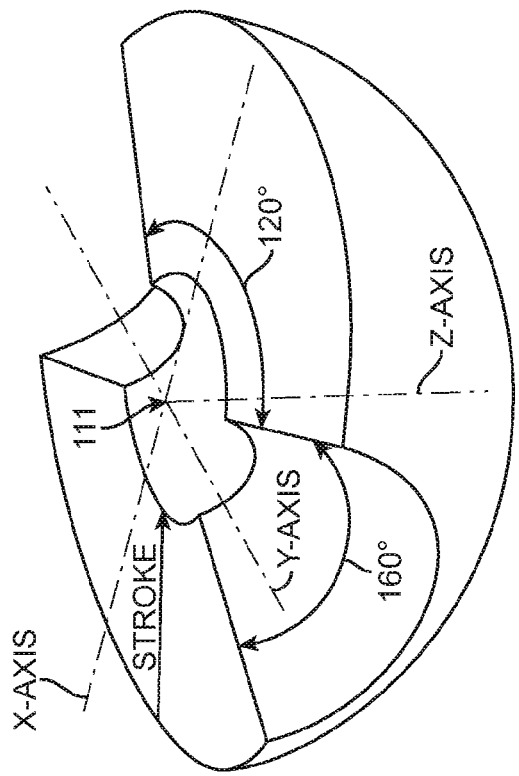
FIG. 6B
FIG. 6A
FIG. 6C

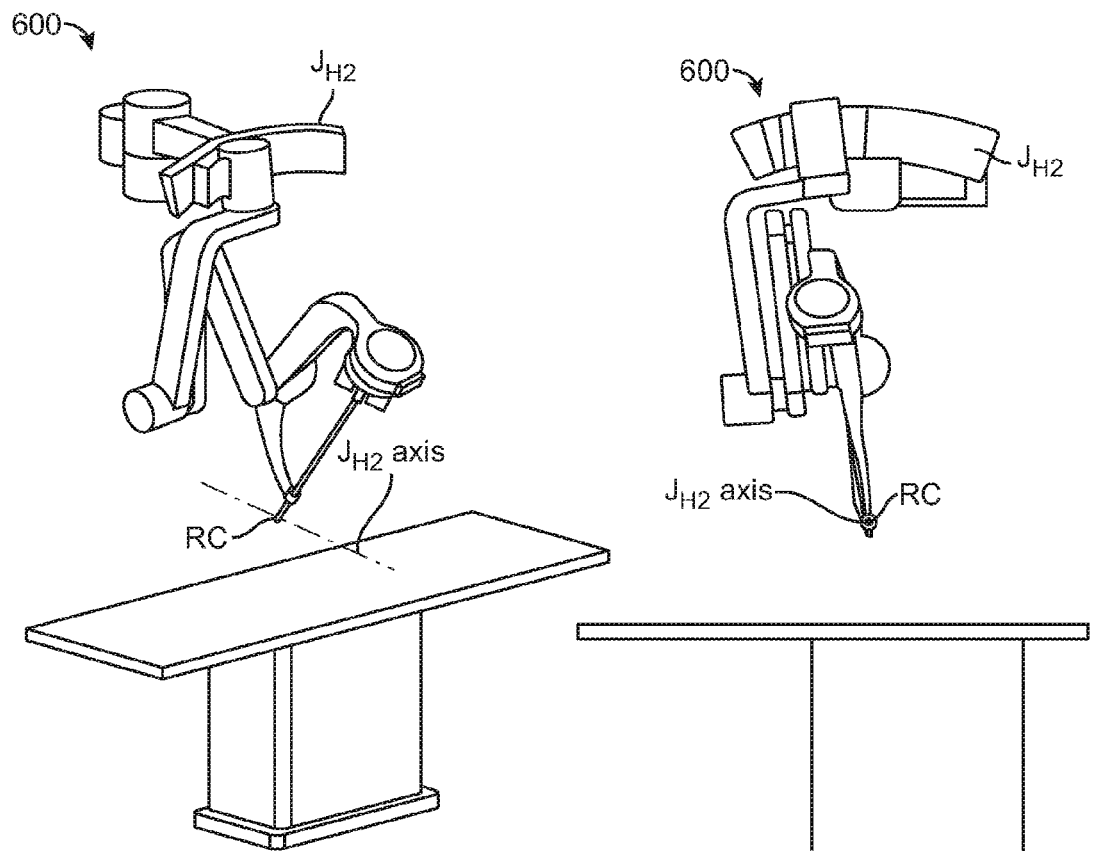
FIG. 13A
FIG. 13B
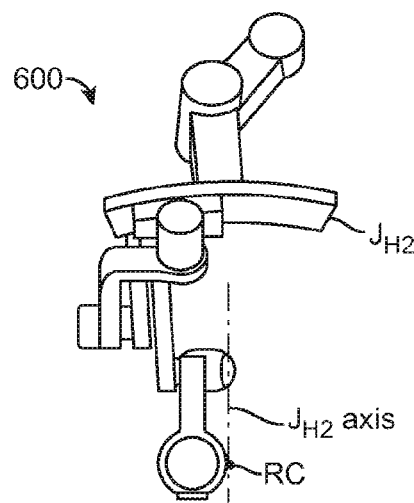
FIG. 13C

SYSTEMS AND METHODS FOR CANCELLATION OF JOINT MOTION USING THE NULL-SPACE

CROSS-REFERENCES TO RELATED APPLICATIONS

This application is a continuation of U.S. patent application Ser. No. 13/967,606, filed on Aug. 15, 2013, and issued as U.S. Pat. No. 9,107,683, on Aug. 18, 2015, which claims the benefit of priority from U.S. Provisional Patent Application No. 61/683,638 filed on Aug. 15, 2012, and entitled "Systems and Methods for Cancellation of Joint Motion Using the Null-Space", the full disclosures of which are incorporated herein by reference in their entireties.

The present application is generally related to the following commonly-owned applications: U.S. application Ser. No. 12/494,695 filed Jun. 30, 2009, entitled "Control of Medical Robotic System Manipulator About Kinematic Singularities;" U.S. application Ser. No. 12/406,004 filed Mar. 17, 2009, entitled "Master Controller Having Redundant Degrees of Freedom and Added Forces to Create Internal Motion;" U.S. application Ser. No. 11/133,423 filed May 19, 2005 (U.S. Pat. No. 8,004,229), entitled "Software Center and Highly Configurable Robotic Systems for Surgery and Other Uses;" U.S. application Ser. No. 10/957,077 filed Sep. 30, 2004 (U.S. Pat. No. 7,594,912), entitled "Offset Remote Center Manipulator For Robotic Surgery;" and U.S. application Ser. No. 09/398,507 filed Sep. 17, 1999 (U.S. Pat. No. 6,714,839), entitled "Master Having Redundant Degrees of Freedom;" U.S. Provisional Application No. 61/654,755 filed Jun. 1, 2012, entitled "Manipulator Arm-to-Patient Collision Avoidance Using a Null-Space;" and U.S. Provisional Application No. 61/654,773 filed Jun. 1, 2012, entitled "System and Methods for Avoiding Collisions Between Manipulator Arms Using a Null-Space," the disclosures of which are incorporated herein by reference in their entireties.

BACKGROUND OF THE INVENTION

The present invention generally provides improved surgical and/or robotic devices, systems, and methods.

Minimally invasive medical techniques are aimed at reducing the amount of tissue that is damaged during diagnostic or surgical procedures, thereby reducing patient recovery time, discomfort, and deleterious side effects. Millions of "open" or traditional surgeries are performed each year in the United States; many of these surgeries can potentially be performed in a minimally invasive manner. However, only a relatively small number of surgeries currently use minimally invasive techniques due to limitations in surgical instruments, and techniques, and the additional surgical training required to master them.

Minimally invasive telesurgical systems for use in surgery are being developed to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing typically a three-dimensional image of the surgical site on a suitable viewer or display, the surgeon performs the surgical procedures on the patient by manipulating master control input devices, which in turn control the motion of robotic instruments. The robotic surgical instruments can be inserted through small, minimally invasive surgical apertures to treat tissues at surgical sites within the patient, often the trauma associated with accessing for open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

The servomechanism used for telesurgery will often accept input from two master controllers (one for each of the surgeon's hands) and may include two or more robotic arms or manipulators. Mapping of the hand movements to the image of the robotic instruments displayed by the image capture device can help provide the surgeon with accurate control over the instruments associated with each hand. In many surgical robotic systems, one or more additional robotic manipulator arms are included for moving an endoscope or other image capture device, additional surgical instruments, or the like.

A variety of structural arrangements can be used to support the surgical instrument at the surgical site during robotic surgery. The driven linkage or "slave" is often called a robotic surgical manipulator, and example linkage arrangements for use as a robotic surgical manipulator during minimally invasive robotic surgery are described in U.S. Pat. Nos. 6,758,843; 6,246,200; and 5,800,423, the full disclosures of which are incorporated herein by reference. These linkages often make use of a parallelogram arrangement to hold an instrument having a shaft. Such a manipulator structure can constrain movement of the instrument so that the instrument shaft pivots about a remote center of spherical rotation positioned in space along the length of the rigid shaft. By aligning this center of rotation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially dangerous forces against the abdominal wall. Alternative manipulator structures are described, for example, in U.S. Pat. Nos. 6,702,805; 6,676,669; 5,855,583; 5,808,665; 5,445,166; and 5,184,601, the full disclosures of which are incorporated herein by reference.

While the new robotic surgical systems and devices have proven highly effective and advantageous, still further improvements would be desirable. For example, a manipulator arm may include additional redundant joints to provide increased movements or configurations under certain conditions. When moving surgical instruments within a minimally invasive surgical site, however, these joints may exhibit a significant amount of movement outside the patient, often more movement than needed or expected, particularly when pivoting instruments about minimally invasive apertures through large angular ranges. Alternative manipulator structures have been proposed which employ software control over a highly configurable kinematic manipulator joint set to restrain pivotal motion to the insertion site while inhibiting inadvertent manipulator/manipulator contact outside the patient (or the like). These highly configurable "software center" surgical manipulator systems may provide significant advantages, but may also present challenges. In particular, the mechanically constrained remote-center linkages may have safety advantages in some conditions. Additionally, the wide range of configurations of the numerous joints often included in these manipulators may result in the manipulators being difficult to manually set-up in a configuration that is desirable for a particular procedure. Nonetheless, as the range of surgeries being performed using telesurgical systems continues to expand, there is an increasing demand for expanding the available configurations and the range of motion of the instruments within the patient. Unfortunately, both of these changes can increase the challenges associated with the motion of the manipulators outside the body and can also increase the importance of avoiding unnecessary movement of the manipulators arm for certain tasks.

For these and other reasons, it would be advantageous to provide improved devices, systems, and methods for surgery, robotic surgery, and other robotic applications. It would be particularly beneficial if these improved technologies provided the ability to limit the amount of movement of the manipulator arm during certain tasks. Additionally, it would be desirable to provide such improvements while increasing the range of motion of the instruments for at least some tasks and without significantly increasing the size, mechanical complexity, or costs of these systems, and while maintaining or improving their dexterity.

BRIEF SUMMARY OF THE INVENTION

The present invention generally provides improved robotic and/or surgical devices, systems, and methods. In various embodiments, the invention will employ highly configurable surgical robotic manipulators. These manipulators, for example, may have more degrees of freedom of movement than the associated surgical end effectors have within a surgical workspace. A robotic surgical system in accordance with the present invention typically includes a manipulator arm supporting a robotic surgical instrument and a processor to calculate coordinated joint movements for manipulating an end effector of the instrument. The joints of the robotic manipulators supporting the end effectors allow the manipulator to move throughout a range of different configurations for a given end effector position and/or a given pivot point location. A manipulator may include additional redundant joints to allow for various types of movement, such as a reconfiguration movement in response to a user command or an auxiliary movement, particularly a collision avoidance movement. The invention allows for cancellation of movement of one or more joints of a non-moving subset of joints of the manipulator arm (also referred to as a "locked" set of joints) to effect a first task, such as a desired end effector movement, while concurrently allowing movement of the one or more joints of the non-moving subset for another task, such as a reconfiguration movement or an auxiliary movement. It should be noted that the non-moving subset (or locked set) of joints are not required to be mechanically "locked" to constrain movement, but rather can be effectively locked by utilizing the methods described herein to provide the "non-moving" or "locked" aspect of the joints. The terms "locked" and "non-moving" (e.g. "non-moving subset" or "locked set" of joints) are used interchangeably throughout.

In general, commanded movement of the manipulator arm to effect movement of the distal end effector utilizes movement of all the joints of the manipulator arm. Although the reconfiguration movement may utilize the same joints as used in manipulation of the end effector, it may be desirable for one or more of the joints of the manipulator arm to remain locked when effecting certain types of movement, such as commanded manipulation movement of the end effector. Additionally, it may be advantageous to allow movement of the one or more "locked" or "non-moving" joints to effect certain other tasks, such as reconfiguration or various auxiliary tasks based on an autonomous algorithm, such as a collision avoidance movement of the manipulator arm. In some embodiments, the system calculates a cancellation movement for the plurality of joints to cancel the movement of one or more joints of a "locked set" or "non-moving subset" of joints for which no movement is desired to effect a particular task. In certain aspects, the system allows for motion cancellation of the desired joints, at least for certain commanded movement, and may allow movement of the locked joints in certain other movements by overlaying the other movements over the joint cancellation movement.

In certain embodiments, a system operator enters a reconfiguration command with a user input device and drives one or more joints of the manipulator within the null-space until the manipulator is reconfigured as desired. In some embodiments, the system effects a collision avoidance movement to avoid a patient surface or an obstacle such as an adjacent manipulator arm. The system may utilize the motion cancellation scheme described above for the plurality of joints to cancel movement of one or more joints of a locked set of joints of the manipulator arm with respect to a particular type of movement, such as a commanded end effector manipulation movement, while allowing movement of the one or more joints with respect to one or more of the various other types of movement described herein.

In certain aspects of the present invention, a redundant degrees of freedom (RDOF) surgical robotic system with manipulate input is provided. The RDOF surgical robotic system comprises a manipulator assembly, one or more user input devices, and a processor with a controller. A manipulator arm of the assembly has a plurality of joints providing sufficient degrees of freedom that allow a range of joint states for a given end effector state. In response to a received reconfiguration command entered by a user, the system calculates velocities of the plurality of joints within a null-space. The joints are driven according to the reconfiguration command and the calculated movement so as to maintain the desired state of the end effector. In response to receiving a manipulation command to move the end effector with a desired movement, the system calculates end effector displacing movement of the joints by calculating joint velocities within a null-perpendicular-space of the Jacobian orthogonal to the null-space, and drives the joints according to the calculated movement to effect the desired end effector movement. To provide increased range of motion for the various other types of movements described above, the system may include a revolute proximal most joint and/or a distal revolute joint coupling an instrument to a proximal portion of the manipulator arm. If a user desires that one or both of these joints not be driven, moved or effectively "locked out" to effect end effector manipulation, the system may detect the movement calculated for those joints to effect a commanded end effector manipulation and calculate an cancellation movement opposing the calculated movement so that when driven according to the combined end effector displacing movement and cancellation movement, the manipulator arm provides the desired end effector manipulation without driving the locked out joint(s) to effect the manipulation movement.

In another aspect of the present invention, the manipulator is configured to move such that an intermediate portion of the instrument shaft pivots about a remote center. Between the manipulator and the instrument, there are a plurality of driven joints providing sufficient degrees of freedom to allow a range of joint states for an end effector position when the intermediate portion of the instrument shaft passes through an access site. A processor having a controller couples the input device to the manipulator. In response to a reconfiguration command, the processor determines movements of one or more joints to effect the desired reconfiguration so that the intermediate portion of the instrument is within the access site during the end effector's desired movement and maintains the desired remote center location about which the shaft pivots. In various embodiments, in response to receiving a manipulation command to effect a desired end effector's movement, the system calculates end effector displacing movement of the joints, comprising calculating joint velocities within a null-perpendicular-space of the Jacobian orthogonal to the null-space, and drives the joints according to the calculated movement to effect the desired end effector movement in which the instrument shaft pivots about the remote center.

In certain aspects, a joint from the first set of joints of the manipulator is a revolute joint coupling the manipulator arm to the base. The desired state of the end effector may include a desired position, velocity or acceleration of the end effector. Generally, the manipulation command and the reconfiguration command are separate inputs that can be received from separate users on separate input devices. However, in some embodiments, these separate inputs are received from the same user. In certain embodiments, the end effector manipulation command is received from an input device by a first user, such as a surgeon entering the command on a surgical console master input, while the reconfiguration command is received from an input device by a second user on a separate input device, such as a physician's assistant entering the reconfiguration command on a patient side cart input device. In some embodiments, the end effector manipulation command and the reconfiguration command are both received by the same user from input devices at a surgical console. In other embodiments, the end effector manipulation command and the reconfiguration command are both received by the same user from input devices at a patient side cart.

In certain aspects, the proximal portion of the manipulator arm is attached to the base such that movement of the proximal portion relative to the base is inhibited while the joints are driven. In some embodiments, the proximal portion is coupled to the base by a joint such that the proximal portion of the manipulator arm is moveable relative to the base while the joints are driven. The joint coupling the proximal portion of the manipulator to the base may be a revolute joint that supports the manipulator arm such that joint movement of the revolute joint pivots one or more joints of the manipulator arm about a pivotal axis of the revolute joints. In various embodiments, the pivotal axis of the revolute joint extends from the joints through a remote center about which an instrument shaft of the end effector pivots. In certain aspects, movement of the revolute pivots one or more joints of the manipulator arm about a cone distally tapered and oriented towards the distal end effector, typically at or near the remote center. The cone around which the manipulator arm pivots in this aspect, corresponds to a cone shaped void within the range of motion of the tool tip, in which the movement of the tool may be impossible or impaired, discussed in further detail below.

In another aspect, the joint coupling the proximal portion of the manipulator to the base is moveable relative to the base along a path, such as an arcuate or substantially circular path such that movement of the joint along the path pivots one or more joints of the manipulator arm about an axis extending through a distal portion of the manipulator arm near the instrument, such as through a remote center about which the instrument shaft pivots. In some embodiments, the manipulator includes a revolute joint coupling the proximal portion of the manipulator to the base, the revolute joint being moveable relative to the base along a path, which may be linear, arcuate or substantially circular.

In yet another aspect of the present invention, a surgical robotic manipulator with a proximal revolute joint and a distal parallelogram linkage is provided, the pivotal axis of the revolute joint substantially intersecting with the axis of the instrument shaft of the end effector, preferably at or near a remote center if applicable. The system further includes a processor having a controller coupling the input to the manipulator arm and configured to calculate a movement of the plurality of joints in response to a user input command. The system may further include an input device for receiving a reconfiguration command to move a first set of joints of the plurality of joints with a desired reconfiguration movement while maintaining the end effector in the desired state.

A further understanding of the nature and advantages of the present invention will become apparent by reference to the remaining portions of the specification and drawings.

BRIEF DESCRIPTION OF THE DRAWINGS

FIGS. 6A-6B show an example manipulator arm in the pitch forward configuration and pitch back configurations, respectively.

FIG. 6C shows a graphical representation of the range of motion of the surgical instrument tool tip of an example manipulator arm, including a cone of silence or conical tool access limit zone in each of the pitch forward and pitch back configurations.

FIGS. 13A-13C show example manipulator arms having a proximal joint that translates a proximal joint supporting the manipulator arm about a path of the joint.

DETAILED DESCRIPTION OF THE INVENTION

Figure 1A:
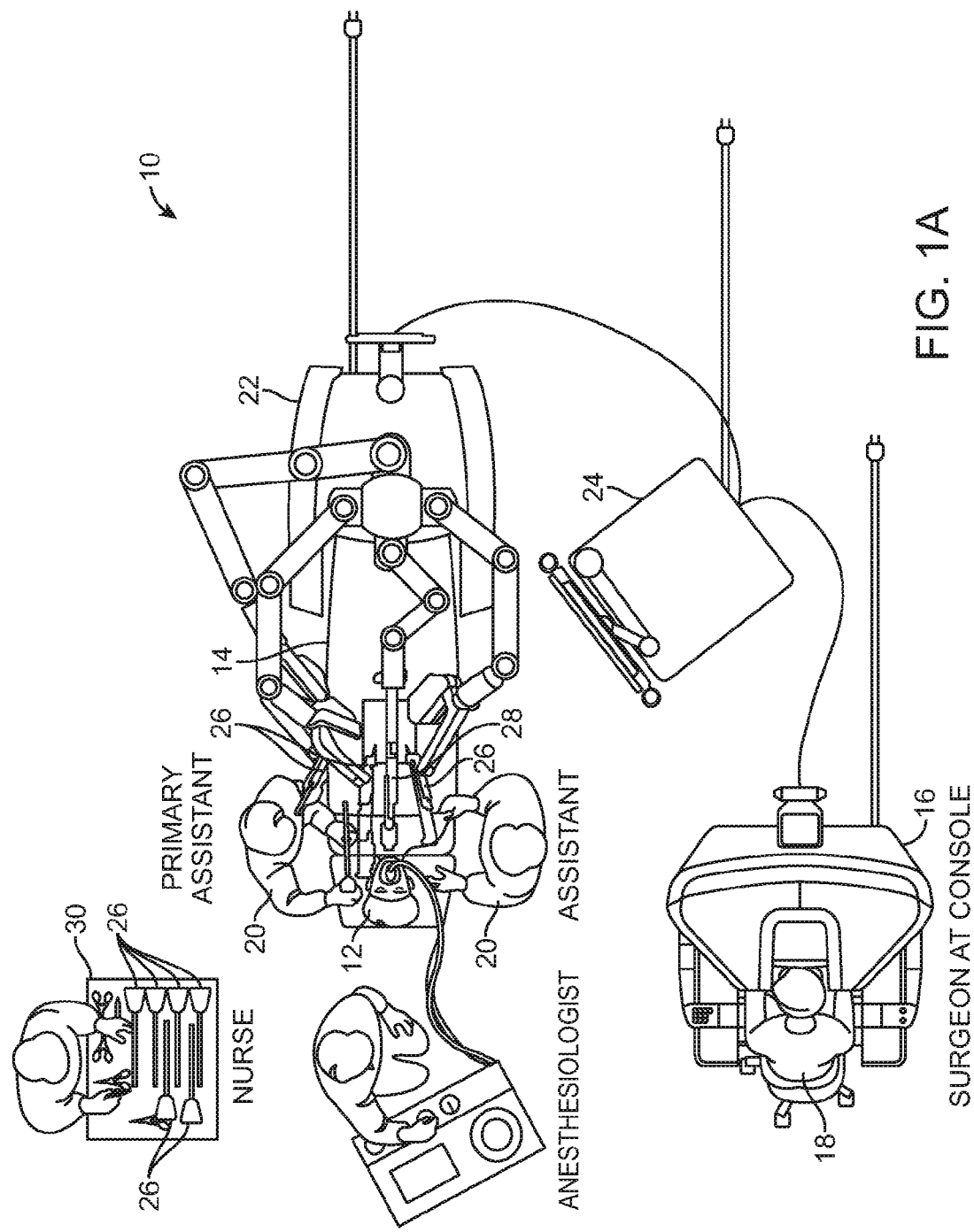
FIG. 1A is an overhead view of a robotic surgical system in accordance with embodiments of the present invention, the robotic surgical system having a surgical station with a plurality of robotic manipulators for robotically moving surgical instruments having surgical end effectors at an internal surgical site within a patient.

The present invention generally provides improved surgical and robotic devices, systems, and methods. The invention is particularly advantageous for use with surgical robotic systems in which a plurality of surgical tools or instruments will be mounted on and moved by an associated plurality of robotic manipulators during a surgical procedure. The robotic systems will often comprise telerobotic, telesurgical, and/or telepresence systems that include processors configured as master-slave controllers. By providing robotic systems employing processors appropriately configured to move manipulator assemblies with articulated linkages having relatively large numbers of degrees of freedom, the motion of the linkages can be tailored for work through a minimally invasive access site. The large number of degrees of freedom allows a system operator, or an assistant, to reconfigure the linkages of the manipulator assemblies while maintaining the desired end effector state, optionally in preparation for surgery and/or while another user maneuvers the end effector during a surgical procedure.

The robotic manipulator assemblies described herein will often include a robotic manipulator and a tool mounted thereon (the tool often comprising a surgical instrument in surgical versions), although the term "robotic assembly" will also encompass the manipulator without the tool mounted thereon. The term "tool" encompasses both general or industrial robotic tools and specialized robotic surgical instruments, with these later structures often including an end effector suitable for manipulation of tissue, treatment of tissue, imaging of tissue, or the like. The tool/manipulator interface will often be a quick disconnect tool holder or coupling, allowing rapid removal and replacement of the tool with an alternate tool. The manipulator assembly will often have a base which is fixed in space during at least a portion of a robotic procedure and the manipulator assembly may include a number of degrees of freedom between the base and an end effector of the tool. Actuation of the end effector (such as opening or closing of the jaws of a gripping device, energizing an electrosurgical paddle, or the like) will often be separate from, and in addition to, these manipulator assembly degrees of freedom.

In various embodiments, the end effector will move in the workspace with between two and six degrees of freedom. As used herein, the term "position" encompasses both location and orientation. Hence, a change in a position of an end effector (for example) may involve a translation of the end effector from a first location to a second location, a rotation of the end effector from a first orientation to a second orientation, or a combination of both. When used for minimally invasive robotic surgery, movement of the manipulator assembly may be controlled by a processor of the system so that a shaft or intermediate portion of the tool or instrument is constrained to a safe motion through a minimally invasive surgical access site or other aperture. Such motion may include, for example, axial insertion of the shaft through the aperture site into a surgical workspace, rotation of the shaft about its axis, and pivotal motion of the shaft about a pivot point adjacent the access site.

Many of the example manipulator assemblies described herein have more degrees of freedom than are needed to position and move an end effector within a surgical site. For example, a surgical end effector that can be positioned with six degrees of freedom at an internal surgical site through a minimally invasive aperture may in some embodiments have nine degrees of freedom (six end effector degrees of freedom—three for location, and three for orientation—plus three degrees of freedom to comply with the access site constraints), but may have ten or more degrees of freedom. Highly configurable manipulator assemblies having more degrees of freedom than are needed for a given end effector position can be described as having or providing sufficient degrees of freedom to allow a range of joint states for an end effector position in a workspace. For example, for a given end effector position, the manipulator assembly may occupy (and be driven between) any of a range of alternative manipulator linkage positions. Similarly, for a given end effector velocity vector, the manipulator assembly may have a range of differing joint movement speeds for the various joints of the manipulator assembly within the null-space of the Jacobian.

The invention provides robotic linkage structures which are particularly well suited for surgical (and other) applications in which a wide range of motion is desired, and for which a limited dedicated volume is available due to the presence of other robotic linkages, surgical personnel and equipment, and the like. The large range of motion and reduced volume needed for each robotic linkage may also provide greater flexibility between the location of the robotic support structure and the surgical or other workspace, thereby facilitating and speeding up setup.

The term "state" of a joint or the like will often herein refer to the control variables associated with the joint. For example, the state of an angular joint can refer to the angle defined by that joint within its range of motion, and/or to the angular velocity of the joint. Similarly, the state of an axial or prismatic joint may refer to the joint's axial position, and/or to its axial velocity. While many of the controllers described herein comprise velocity controllers, they often also have some position control aspects. Alternative embodiments may rely primarily or entirely on position controllers, acceleration controllers, or the like. Many aspects of control system that can be used in such devices are more fully described in U.S. Pat. No. 6,699,177, the full disclosure of which is incorporated herein by reference. Hence, so long as the movements described are based on the associated calculations, the calculations of movements of the joints and movements of an end effector described herein may be performed using a position control algorithm, a velocity control algorithm, a combination of both, and/or the like.

In various embodiments, the tool of an example manipulator arm pivots about a pivot point adjacent a minimally invasive aperture. The system may utilize a hardware remote center, such as the remote center kinematics described in U.S. Pat. No. 6,786,896, the entire contents of which are incorporated herein in its entirety. Such systems may also utilize a double parallelogram linkage which constrains the movement of the linkages such that the shaft of the instrument supported by the manipulator pivots about a remote center point. Alternative mechanically constrained remote center linkage systems are known and/or may be developed in the future. Surprisingly, work in connection with the present invention indicates that remote center linkage systems benefit from highly configurable kinematic architectures. In particular when a surgical robotic system has a linkage that allows pivotal motion about two axes intersecting at or near a minimally invasive surgical access site, the spherical pivotal motion may encompass the full extent of a desired range of motion within the patient, but may still suffer from avoidable deficiencies (such as being poorly conditioned, being susceptible to arm-to-arm or arm-to-patient contact outside the patient, and/or the like). At first, adding one or more additional degrees of freedom that are also mechanically constrained to pivotal motion at or near the access site would appear to offer few or any improvements in the range of motion. Nonetheless, such joints can provide significant advantages by allowing the overall system to be configured in or driven toward a collision-inhibiting pose by further extending the range of motion for other surgical procedures, and the like. In other embodiments, the system may utilize software to achieve a remote center, such as described in U.S. Pat. No. 8,004,229, the entire contents of which are incorporated herein by reference. In a system having a software remote center, the processor calculates movement of the joints so as to pivot an intermediate portion of the instrument shaft about a calculated pivot point, as opposed to a pivot point defined by a mechanical constraint. By having the capability to compute software pivot points, different modes characterized by the compliance or stiffness of the system can be selectively implemented. More particularly, different system modes over a range of pivot points/centers (e.g., moveable pivot points, passive pivot points, fixed/rigid pivot point, soft pivot points) can be implemented as desired.

Despite the many advantages of a robotic surgical system having multiple highly configurable manipulators, since the manipulators include a relatively large number of joints and links between the base and instrument, manual positioning of the links can be challenging and complicated. Even when the manipulator structure is balanced so as to avoid gravitational effects, attempting to align each of the joints in an appropriate arrangement or to reconfigure the manipulator as desired can be difficult, time consuming, and may involve significant training and/or skill. The challenges can be even greater when the links of the manipulator are not balanced about the joints, such that positioning such a highly configurable structures in an appropriate configuration before or during surgery can be a struggle due to the manipulator arm length and the passive and limp design in many surgical systems.

These issues can be addressed by allowing a user, such as a physician's assistant, to quickly and easily reconfigure the manipulator arm, while and maintaining the desired end effector state, optionally even during movement of the end effector during a surgical procedure. One or more additional joints may be included in the manipulator arm to increase the range of motion and configurations of the manipulator arm to enhance this capability. While providing additional joints may provide increased range of motion for certain tasks, the large number of redundant joints in the manipulator arm may cause various movements of the arm to be overly complex for other tasks, such that the movements appear unpredictable or the amount of overall movements causes various other clinical concerns. It may further be useful to cancel movement of the one or more joints for which no movement is desired for a first task (referred to herein as "locked" joints or a "locked set of joints") while allowing movement of the locked set of joints for various other tasks that may be performed concurrently with the first task. Locking out certain joints without actually physically constraining movement of the locked out joints is advantageous since movement of the locked out joints may be desired to effect other tasks or movements. In various embodiments, the invention further allows for the desired motion cancellation of the one or more joints in a non-moving subset (or locked set) of joints while still allowing movement of the locked set of joints for various other movements, such as movements based on autonomous algorithms or a commanded reconfiguration movement.

In certain aspects, a commanded end effector movement within a surgical space is effected by driving one or more joints of the manipulator according to a coordinated end effector displacing movement of the joints calculated by a processor within a null-space-perpendicular of the kinematic Jacobian. Various other tasks, such as a reconfiguration movement or an auxiliary task such as a collision avoidance movement, may be effected while maintaining the desired state of the end effector by driving one or more joints of the manipulator according to coordinated movement of the joints calculated within a null-space of the Jacobian, often concurrent with the end effector displacing movement.

In some embodiments, calculated movement relating to various other tasks, such as an avoidance movement based on an autonomous algorithm, may overlay the cancellation movement so that he "locked joints" can still be moved to effect the various other tasks. Examples of such avoidance movement are described in U.S. Provisional Application No. 61/654,755 filed Jun. 1, 2012, entitled "Manipulator Arm-to-Patient Collision Avoidance Using a Null-Space;" and U.S. Provisional Application No. 61/654,773 filed Jun. 1, 2012, entitled "System and Methods for Avoiding Collisions Between Manipulator Arms Using a Null-Space," the disclosures of which are incorporated herein by reference in their entireties. The calculated movement that overlays the cancelled movement of the "locked out" joints, however, is not limited to the autonomous movement and may include various other movements, such as a commanded reconfiguration movement or various auxiliary movements.

Embodiments of the invention may include a user input which is configured to take advantage of the degrees of freedom of a manipulator structure. Rather than manually reconfiguring the manipulator, the input facilitates use of driven joints of the kinematic linkage to reconfigure the manipulator structure in response to entry of a reconfiguration command by a user. In various embodiments, the user input for receiving the reconfiguration command is incorporated into and/or disposed near the manipulator arm. In other embodiments, the input comprises a centralized input device to facilitate reconfiguration of one or more joints, such as a cluster of buttons on the patient side cart or a joystick. The input device for receiving the reconfiguration command may be separate from the input for receiving a manipulation command to effect movement of the end effector. A controller of the surgical system may include a processor with readable memory having joint controller programming instructions or code recorded thereon which allows the processor to derive suitable joint commands for driving the joints recorded thereon so as to allow the controller to effect the desired reconfiguration in response to entry of the reconfiguration command. It is appreciated, however, that the invention may be used in a manipulator arms with or without a reconfiguration feature.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Referring now to the drawings, in which like reference numerals represent like parts throughout the several views, FIG. 1A is an overhead view illustration of a Minimally Invasive Robotic Surgical (MIRS) system 10, in accordance with many embodiments, for use in performing a minimally invasive diagnostic or surgical procedure on a Patient 12 who is lying down on an Operating table 14. The system can include a Surgeon's Console 16 for use by a surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the surgeon 18 views the surgical site through the Console 16. An image of the surgical site can be obtained by an endoscope 28, such as a stereoscopic endoscope, which can be manipulated by the Patient Side Cart 22 so as to orient the endoscope 28. The Electronics Cart 24 can be used to process the images of the surgical site for subsequent display to the surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 1B:
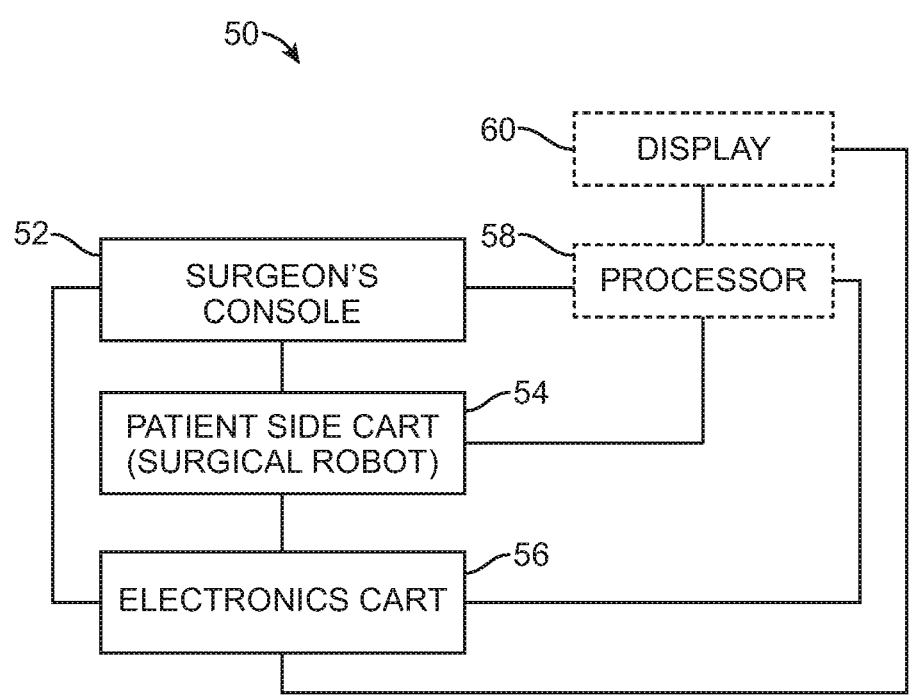
FIG. 1B diagrammatically illustrates the robotic surgical system of FIG. 1A.

FIG. 1B diagrammatically illustrates a robotic surgery system 50 (such as MIRS system 10 of FIG. 1A). As discussed above, a Surgeon's Console 52 (such as Surgeon's Console 16 in FIG. 1A) can be used by a surgeon to control a Patient Side Cart (Surgical Robot) 54 (such as Patent Side Cart 22 in FIG. 1A) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1A). As discussed above, the Electronics Cart 56 can process the captured images in a variety of ways prior to any subsequent display. For example, the Electronics Cart 56 can overlay the captured images with a virtual control interface prior to displaying the combined images to the surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination of the Electronics Cart 56 and the processor 58, which can be coupled together so as to process the captured images jointly, sequentially, and/or in combinations thereof. One or more separate displays 60 can also be coupled with the processor 58 and/or the Electronics Cart 56 for local and/or remote display of images, such as images of the procedure site, or other related images.

Figure 2:
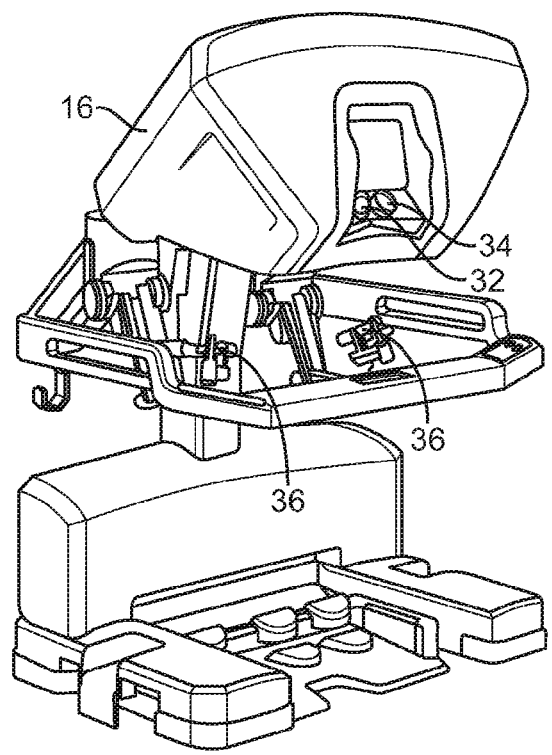
FIG. 2 is a perspective view illustrating a master surgeon console or workstation for inputting surgical procedure commands in the surgical system of FIG. 1A, the console including a processor for generating manipulator command signals in response to the input commands.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1A) to manipulate one or more tools. The input control devices 36 can provide the same degrees of freedom as their associated tools 26 (shown in FIG. 1A) so as to provide the surgeon with telepresence, or the perception that the input control devices 36 are integral with the tools 26 so that the surgeon has a strong sense of directly controlling the tools 26. To this end, position, force, and tactile feedback sensors (not shown) may be employed to transmit position, force, and tactile sensations from the tools 26 back to the surgeon's hands through the input control devices 36.

The Surgeon's Console 16 is usually located in the same room as the patient so that the surgeon may directly monitor the procedure, be physically present if necessary, and speak to an Assistant directly rather than over the telephone or other communication medium. However, the surgeon can be located in a different room, a completely different building, or other remote location from the Patient allowing for remote surgical procedures.

Figure 3:
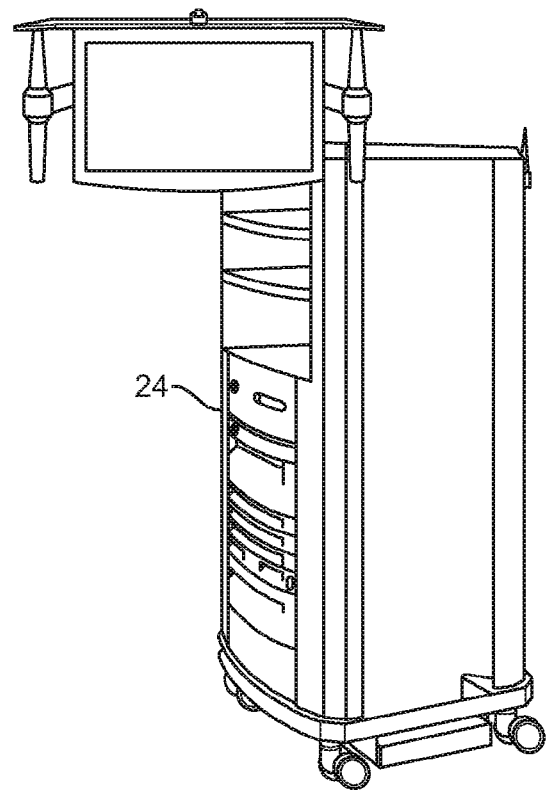
FIG. 3 is a perspective view of the electronics cart of FIG. 1A.

FIG. 3 is a perspective view of the Electronics Cart 24. The Electronics Cart 24 can be coupled with the endoscope 28 and can include a processor to process captured images for subsequent display, such as to a surgeon on the Surgeon's Console, or on another suitable display located locally and/or remotely. For example, where a stereoscopic endoscope is used, the Electronics Cart 24 can process the captured images so as to present the surgeon with coordinated stereo images of the surgical site. Such coordination can include alignment between the opposing images and can include adjusting the stereo working distance of the stereoscopic endoscope. As another example, image processing can include the use of previously determined camera calibration parameters so as to compensate for imaging errors of the image capture device, such as optical aberrations.

Figure 4:
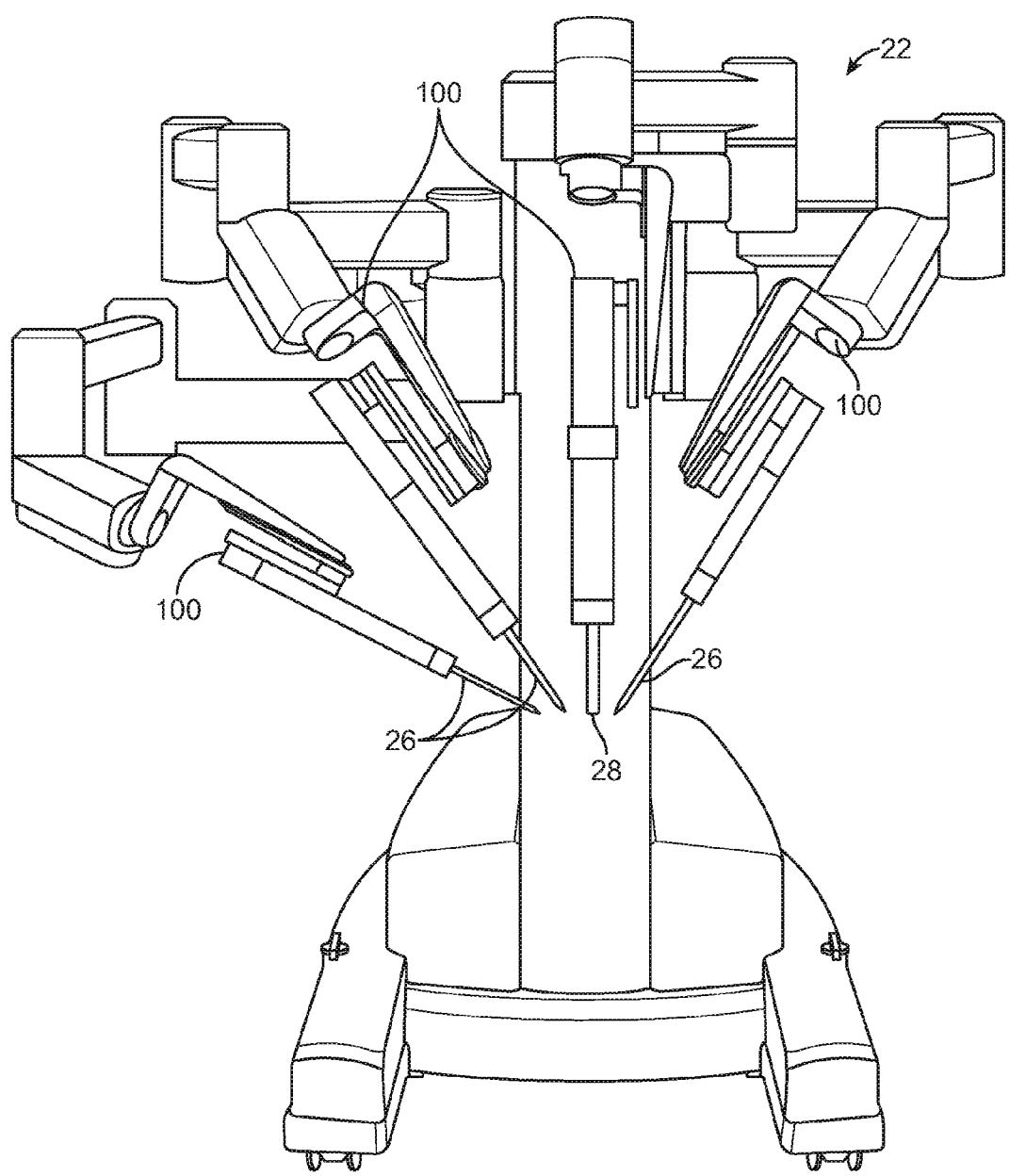
FIG. 4 is a perspective view of a patient side cart having four manipulator arms.

FIG. 4 shows a Patient Side Cart 22 having a plurality of manipulator arms, each supporting a surgical instrument or tool 26 at a distal end of the manipulator arm. The Patient Side Cart 22 shown includes four manipulator arms 100 which can be used to support either a surgical tool 26 or an imaging device 28, such as a stereoscopic endoscope used for the capture of images of the site of the procedure. Manipulation is provided by the robotic manipulator arms 100 having a number of robotic joints. The imaging device 28 and the surgical tools 26 can be positioned and manipulated through incisions in the patient so that a kinematic remote center is maintained at the incision so as to minimize the size of the incision. Images of the surgical site can include images of the distal ends of the surgical instruments or tools 26 when they are positioned within the field-of-view of the imaging device 28.

Regarding surgical tool 26, a variety of alternative robotic surgical tools or instruments of different types and differing end effectors may be used, with the instruments of at least some of the manipulators being removed and replaced during a surgical procedure. Several of these end effectors, including DeBakey Forceps, microforceps, Potts scissors, and clip applier include first and second end effector elements which pivot relative to each other so as to define a pair of end effector jaws. Other end effectors, including scalpel and electrocautery probe have a single end effector element. For instruments having end effector jaws, the jaws will often be actuated by squeezing the grip members of handle. Single end effector instruments may also be actuated by gripping of the grip members, for example, so as to energize an electrocautery probe.

The elongate shaft of instrument 26 allow the end effectors and the distal end of the shaft to be inserted distally into a surgical worksite through a minimally invasive aperture, often through an abdominal wall or the like. The surgical worksite may be insufflated, and movement of the end effectors within the patient will often be effected, at least in part, by pivoting of the instrument 26 about the location at which the shaft passes through the minimally invasive aperture. In other words, manipulators 100 will move the proximal housing of the instrument outside the patient so that shaft extends through a minimally invasive aperture location so as to help provide a desired movement of end effector. Hence, manipulators 100 will often undergo significant movement outside patient P during a surgical procedure.

Example manipulator arms in accordance with many embodiments of the present invention can be understood with reference to FIGS. 5A-13C. As described above, a manipulator arm generally supports a distal instrument or surgical tool and effects movements of the instrument relative to a base. As a number of different instruments having differing end effectors may be sequentially mounted on each manipulator during a surgical procedure (often with the help of a surgical assistant), a distal instrument holder will optionally allow rapid removal and replacement of the mounted instrument or tool. As can be understood with reference to FIG. 4, manipulators are proximally mounted to a base of the patient side cart. In various embodiments, the manipulator arm includes a plurality of linkages and associated joints extending between the base and the distal instrument holder. In certain aspects, an example manipulator includes a plurality of joints having redundant degrees of freedom such that the joints of the manipulator arm can be driven into a range of differing configurations for a given end effector position. This may be the case for any of the embodiments of manipulator arms disclosed herein.

Figure 5A:
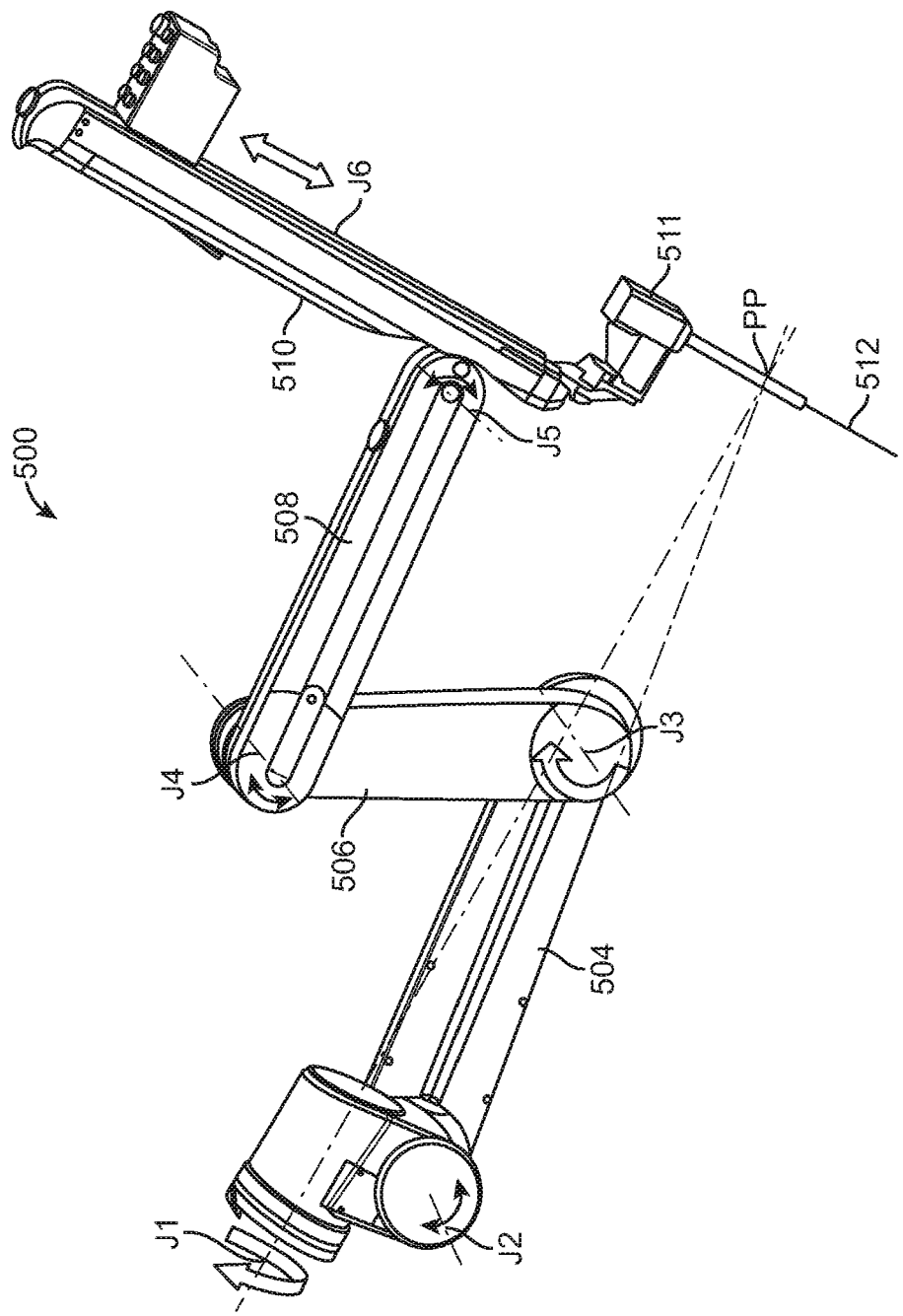
FIGS. 5A-5D show an example manipulator arm.

In certain embodiments, such as shown for example in FIG. 5A, an exemplary manipulator arm includes a proximal revolute joint J1 that rotates about a first joint axis so as to revolve the manipulator arm distal of the joint about the joint axis. In some embodiments, revolute joint J1 is mounted directly to the base, while in other embodiments, joint J1 may be mounted to one or more movable linkages or joints. The joints of the manipulator, in combination, have redundant degrees of freedom such that the joints of the manipulator arm can be driven into a range of differing configurations for a given end effector position. For example, the manipulator arm of FIGS. 5A-5D may be maneuvered into differing configurations while the distal member 511 (such as a cannula through which the tool 512 or instrument shaft extends) supported within the instrument holder 510 maintains a particular state and may include a given position or velocity of the end effector. In various embodiments, distal member 511 is a cannula through which the tool shaft 512 extends, and the instrument holder 510 is a carriage (shown as a brick-like structure that translates on a spar) to which the instrument attaches before extending through the cannula 511 into the body of the patient through the minimally invasive aperture.

Figure 5B:
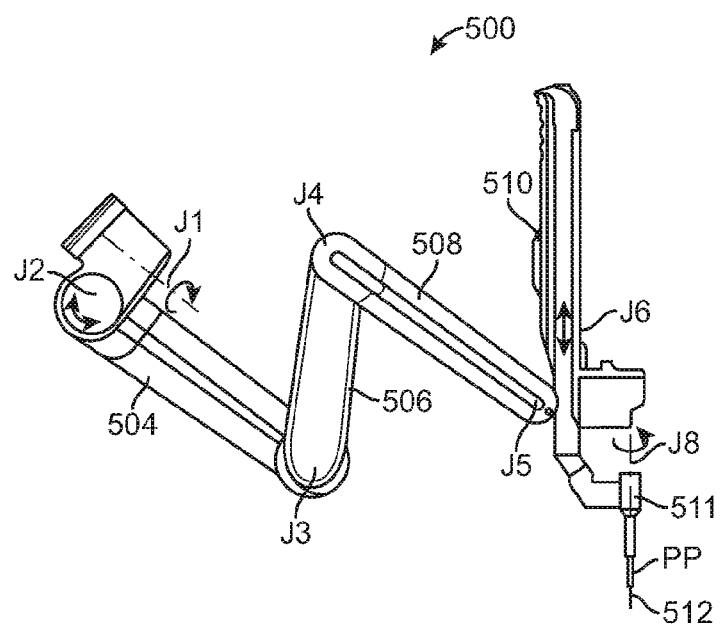
Figure 5D:
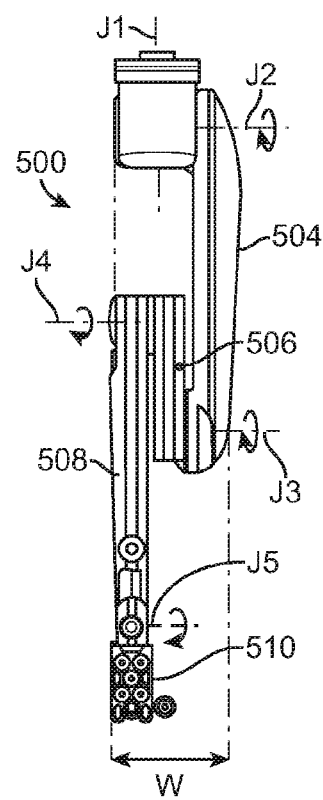
Figure 5C:
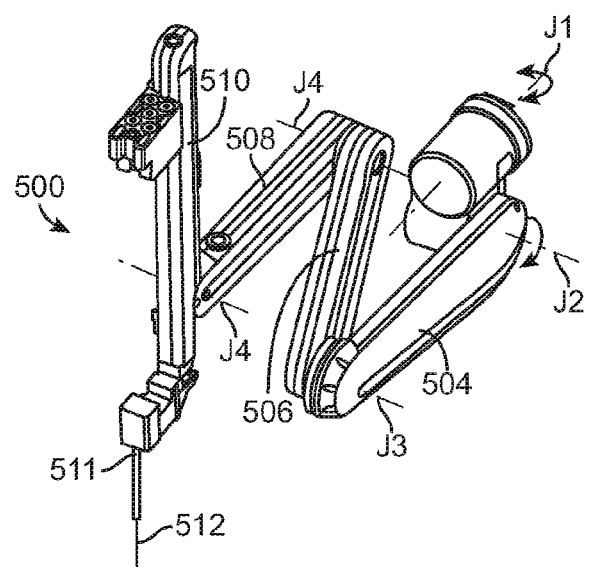

Describing the individual links of manipulator arm 500 of FIGS. 5A-5D along with the axes of rotation of the joints connecting the links as illustrated in FIG. 5A-5D, a first link 504 extends distally from a pivotal joint J2 which pivots about its joint axis and is coupled to revolute joint J1 which rotates about its joint axis. Many of the remainder of the joints can be identified by their associated rotational axes, as shown in FIG. 5A. For example, a distal end of first link 504 is coupled to a proximal end of a second link 506 at a pivotal joint J3 that pivots about its pivotal axis, and a proximal end of a third link 508 is coupled to the distal end of the second link 506 at a pivotal joint J4 that pivots about its axis, as shown. The distal end of the third link 508 is coupled to instrument holder 510 at pivotal joint J5. In various embodiments, the pivotal axes of each of joints J2, J3, J4, and J5 are substantially parallel and the linkages appear "stacked" when positioned next to one another, as shown in FIG. 5D, so as to provide a reduced width w of the manipulator arm and improve patient clearance during maneuvering of the manipulator assembly. In various embodiments, the instrument holder also includes additional joints, such as a prismatic joint J6 that facilitates axial movement of instrument 306 through the minimally invasive aperture and facilitates attachment of the instrument holder to a cannula through which the instrument is slidably inserted.

The distal member or cannula 511 through which the tool 512 extends may include additional degrees of freedom distal of instrument holder 510. Actuation of the degrees of freedom of the instrument will often be driven by motors of the manipulator, and alternative embodiments may separate the instrument from the supporting manipulator structure at a quickly detachable instrument holder/instrument interface so that one or more joints shown here as being on the instrument are instead on the interface, or vice versa. In some embodiments, cannula 511 includes a rotational joint (not shown) near or proximal of the insertion point of the tool tip or the pivot point PP, which generally is disposed at the site of a minimally invasive aperture. A distal wrist of the instrument allows pivotal motion of an end effector of surgical tool 512 about instrument joints axes of one or more joints at the instrument wrist. An angle between end effector jaw elements may be controlled independently of the end effector location and orientation.

The range of motion of an exemplary manipulator assembly can be appreciated by referring to FIGS. 6A-6C. During a surgical procedure, an exemplary manipulator arm can be maneuvered into a pitch forward configuration, as shown in FIG. 6A, or into a pitch back configuration, as shown in FIG. 6B, as needed to access particular patient tissues within a surgical workspace. A typical manipulator assembly includes an end effector that can pitch forwards and backwards about an axis by at least ±60 degrees, preferably by about ±75 degrees, and can also yaw about an axis by ±80 degrees. Although this aspect allows for increased maneuverability of the end effector with the assembly, there may be configurations in which movement of the end effector may be limited, particularly when the manipulator arm is in the full pitch forward or full pitch back configuration as in FIGS. 6A and 6B. In one embodiment, the manipulator arm has a Range of Motion (ROM) of (+/−75 deg) for the outer pitch, and (+/−300 degrees) for the outer yaw joints, respectively. In some embodiments, the ROM may be increased for the outer pitch to provide a ROM larger than (+/−90 deg) in which case the "cone of silence" could be made to disappear entirely, although generally the inner sphere associated with insertion limitations would remain. It is appreciated that various embodiments may be configured to have increased or decreased ROM, that the above noted ROMs are provided for illustrative purposed, and further that the invention is not limited to the ROMs described herein.

FIG. 6C graphically represents the overall range of motion and workspace of the tool tip of the exemplary manipulator of FIGS. 5A-5B. Although the workspace is shown as hemisphere, it may also be represented as a sphere depending on the range of motion and configuration of one or more revolute joints of the manipulator, such as joint J1. As shown, the hemisphere in FIG. 6C includes a central, small spherical void as well as two conical voids. The voids represent the areas in which movement of the tool tip may be impossible due to mechanical constraints or unfeasible due to extremely high joint velocities that make movement of the end effector difficult or slow. For these reasons, the conical void are referred to as the "cone of silence." In some embodiments, the manipulator arm may reach a singularity at a point within the cone. Since movement of the manipulator within or near the cone of silence may be impaired, it can be difficult to move the manipulator arm away from the cone of silence without manually moving one or more links of the manipulator to reconfigure the links and joints as desired, which often requires an alternative operating mode and delays the surgical procedure.

In various embodiments, movement of the instrument shaft into or near these conical portions generally occurs when the angle between distal linkages in the manipulator is relatively small. Such configurations can be avoided by reconfiguring the manipulator to increase the angles between linkages (so that the linkages are moved into a more orthogonal position relative to each other). For example, in the configurations shown in FIGS. 6A and 6B, when the angle between the distal most link and the instrument holder (angle a) becomes relatively small movement of the manipulator may become more difficult. Depending on the range of joint movements in the remaining joints in various embodiments, when the angle between certain linkages decreases, movement of the manipulator may be inhibited and in some cases, the manipulator arm may no longer be redundant. A manipulator configuration in which the instrument shaft nears these conical portions, or in which the angles between linkages are relatively low is said to be "poorly conditioned" such that maneuverability and dexterity of the manipulator arm is limited. It is desirable that the manipulator be "well conditioned" so as to maintain dexterity and range of movement. In certain aspects, the present invention allows a user to avoid movement of the instrument shaft near the above described conical portions by simply entering a command to reconfigure the manipulator as desired, even during movement of the end effector in a surgical procedure. This aspect is particularly useful should the manipulator, for whatever reason, become "poorly conditioned."

While the embodiments of the manipulator described above may be utilized in the present invention, some embodiments may include additional joints, which may also be used to improve dexterity and the conditioning of the manipulator arm. For example, an exemplary manipulator may include a revolute joint and/or linkage proximal of joint J1 which can be used to revolve the manipulator arm of FIG. 5A, and its associated cone of silence, about an axis of the revolute joint so as to reduce or eliminate the cone of silence. In another embodiment, the exemplary manipulator may also include a distal pivotal joint that pivots the instrument holder about an axis substantially perpendicular to joint J5, thereby offsetting the tool tip so as to further reduce the cone of silence and improve the range of movement of the surgical tool. In still another embodiment, a proximal joint of the manipulator arm, such as J1, may be movably mounted on the base, so as to move or shift the cone of silence as needed and improve the range of motion of the manipulator tool tip. The use and advantages of such additional joints can be understood by referring to FIGS. 7A-13C, which illustrate examples of such joints, which may each be used independently of one another or used in combination, in any of the exemplary manipulator arms described herein.

Figure 7A:
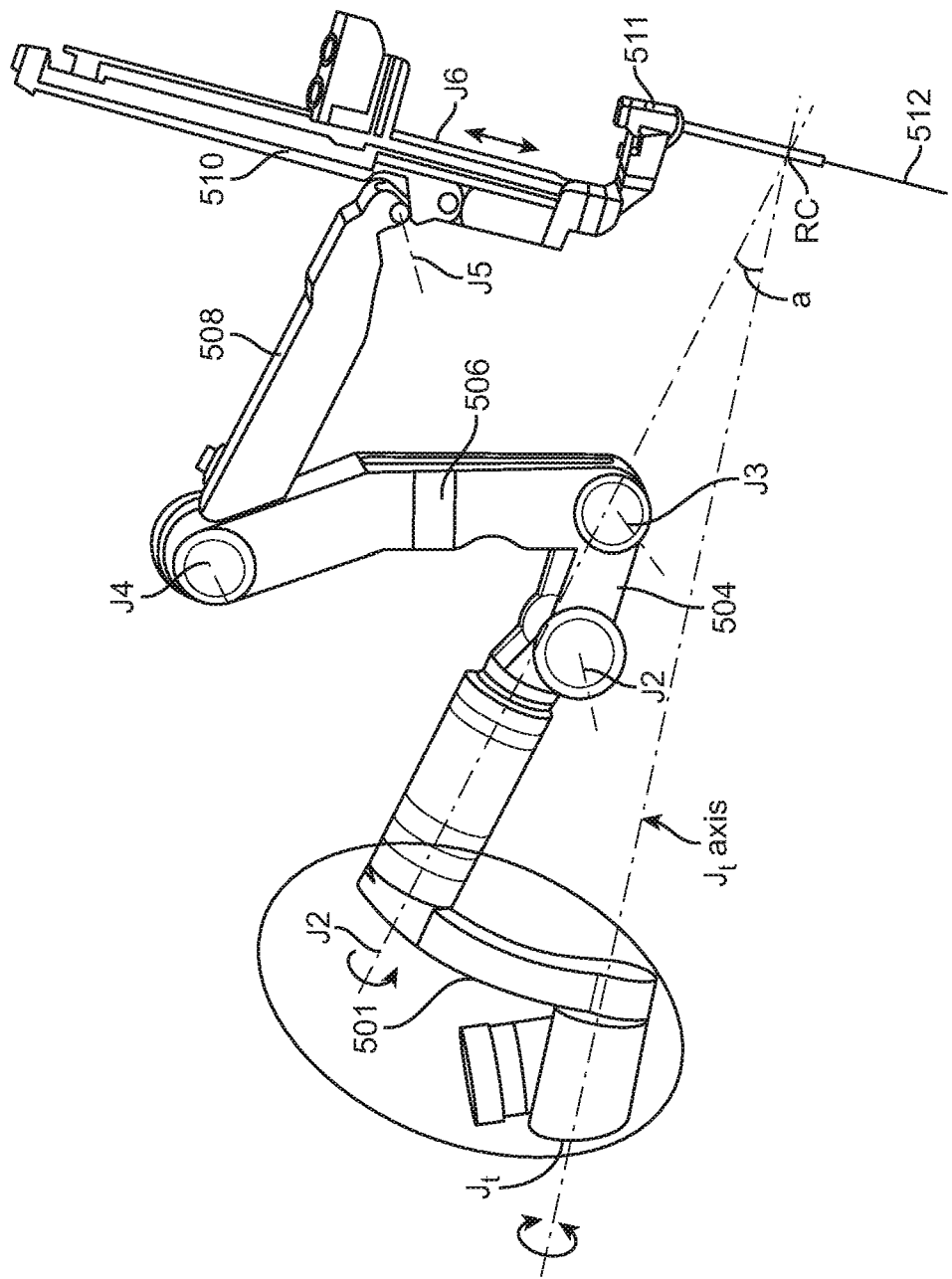
FIG. 7A shows example manipulator arms having a proximal revolute joint that revolves the manipulator arm about an axis of a proximal revolute joint.
Figure 7B:
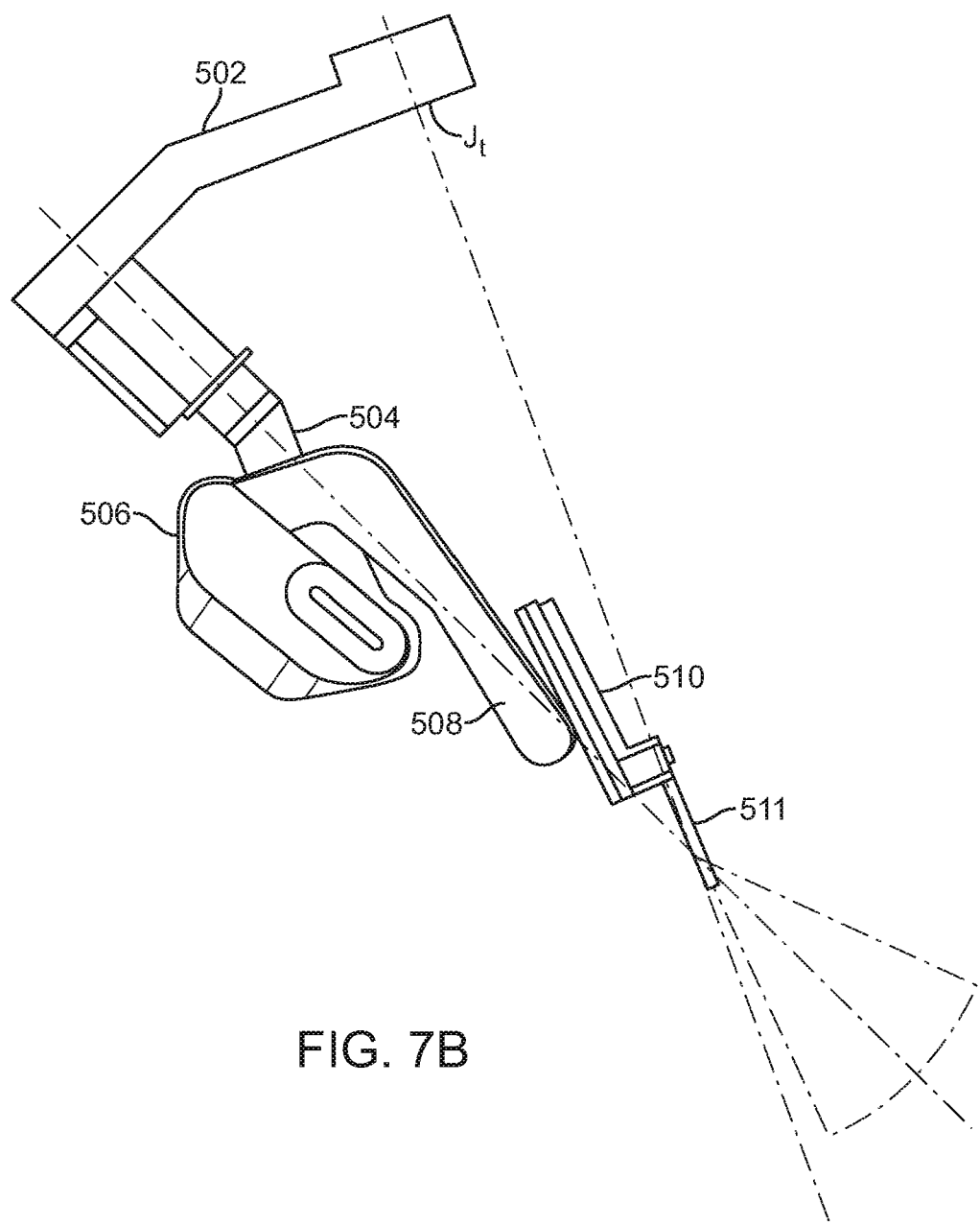
FIG. 7B shows an example manipulator arm and the associated range of motion and cone of silence, the example manipulator arm having a proximal revolute joint that revolves the manipulator arm around an axis of a proximal revolute joint the movement of which can be used to mitigate the depicted cone of silence.

FIGS. 7A-7B illustrate an additional redundant joint for use with exemplary manipulator arms—a first joint coupling a proximal portion of the manipulator arm to the base. The first joint is a proximal revolute joint $J_t$ that revolves the manipulator arm about a joint axis of joint $J_t$. The proximal revolute joint $J_t$ includes a link 501 that offsets joint $J_t$ from the proximal revolute joint $J_t$ by a pre-determined distance or angle. The link 501 can be a curved linkage, as shown in FIG. 7A, or a linear or angled linkage 502, as shown in FIG. 7B. The joint axis of the joint $J_t$ may be aligned with the remote center RC or insertion point of the tool tip, as shown in the embodiment of FIG. 7A. In various embodiments, the joint axis of joint $J_t$ passes through the remote center, as does each other revolute joint axis in the manipulator arm, to prevent motion at the body wall and can therefore be moved during surgery. The axis of joint $J_t$ is coupled to a proximal portion of the arm so it can be used to change the position and orientation of the back of the arm. In general, redundant axes, such as this, allow the instrument tip to follow the surgeon's commands while simultaneously avoiding collisions with other arms or patient anatomy. In certain aspects, the proximal revolute joint $J_t$ is used solely to change the mounting angle of the manipulator with respect to the floor. This angle is important in order to 1) avoid collisions with external patient anatomy and 2) reach anatomy inside the body. In various embodiments, the angle a between the proximal link of the manipulator attached to the proximal revolute joint $J_t$ and the axis of the proximal revolute is about 15 degrees.

FIG. 7B illustrates the relationship of the proximal revolute joint $J_t$ and its associated joint axis and the cone of silence in an exemplary manipulator arm. The joint axis of the proximal revolute joint $J_t$ may pass through the cone of silence or may be completely outside of the cone of silence. By revolving the manipulator arm about the axis of the proximal revolute the cone of silence can be reduced (in an embodiment where the joint $J_t$ axis passes through the cone of silence), or can be effectively eliminated (in an embodiment where the proximal revolute joint axis extends completely outside the cone of silence). The distance and angle of the link 501 determines the position of the joint $J_t$ axis relative to the cone of silence.

Figure 8:
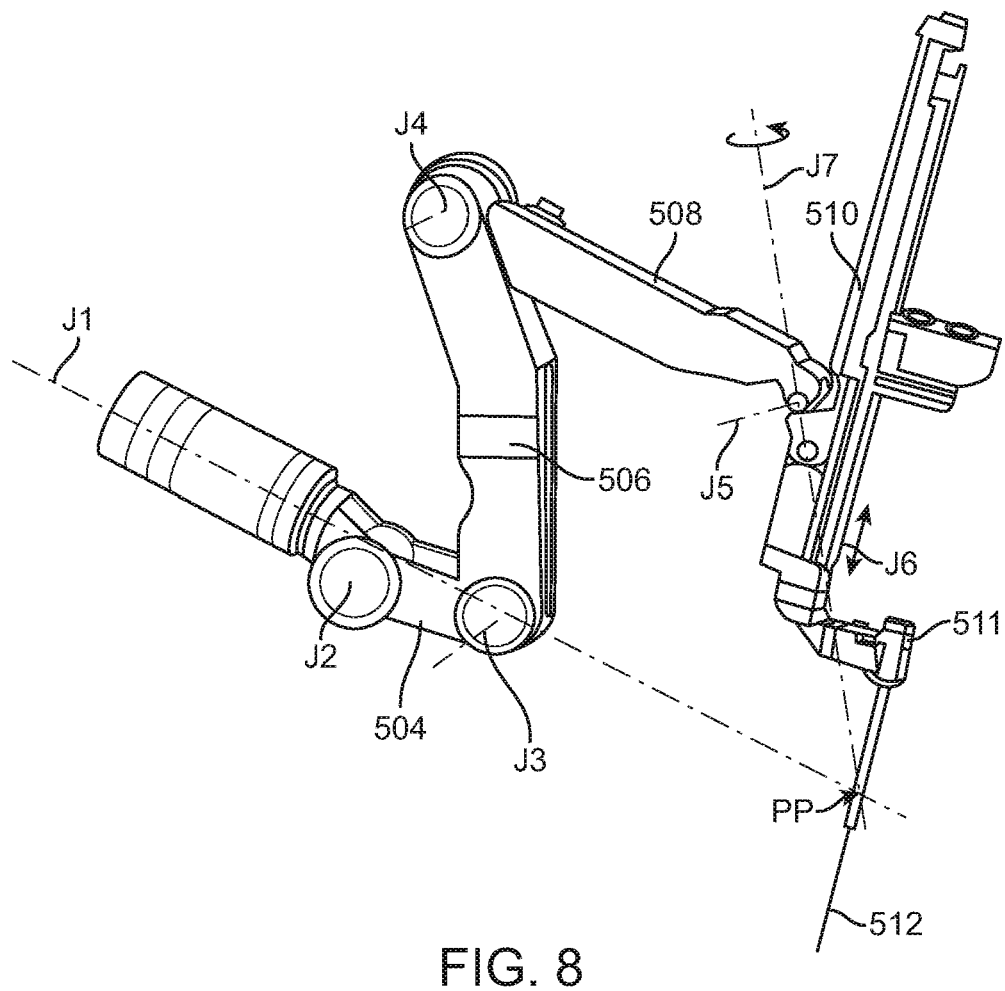
FIG. 8 shows an example manipulator arm having a revolute joint near the distal instrument holder.
Figure 9:
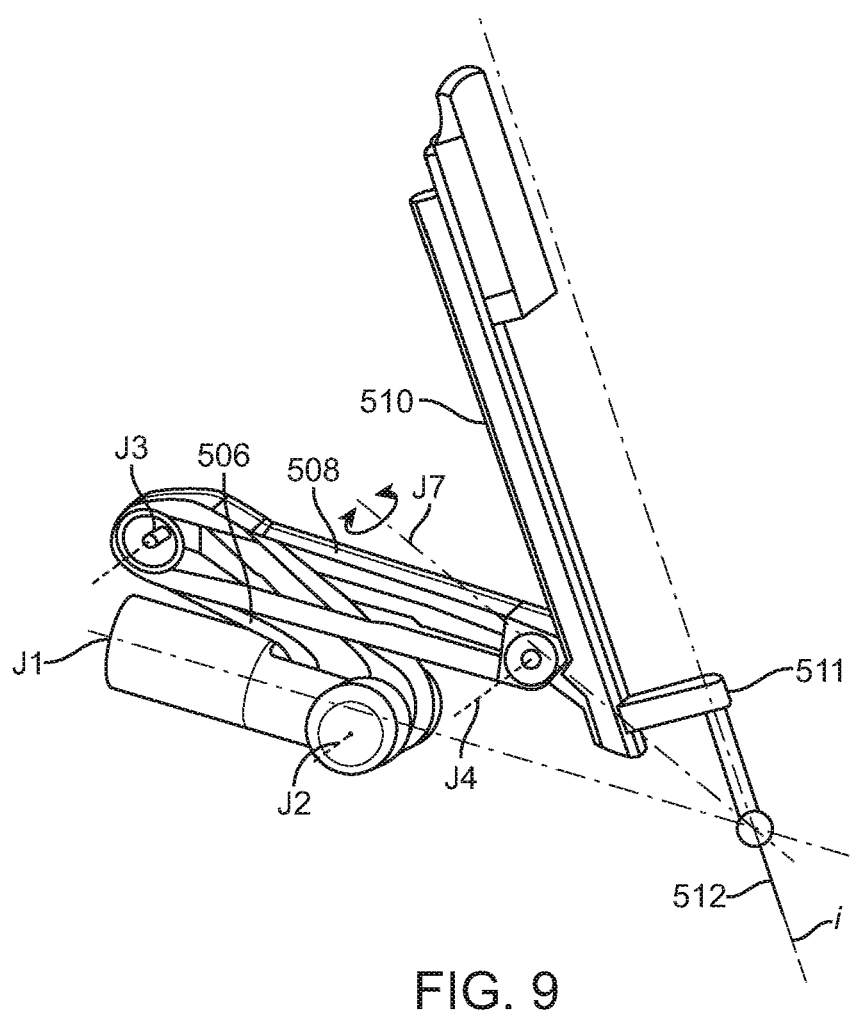
FIG. 9 shows an example manipulator arm having a revolute joint near the distal instrument holder that revolves or twists the instrument holder about the joint axis.
Figure 10A:
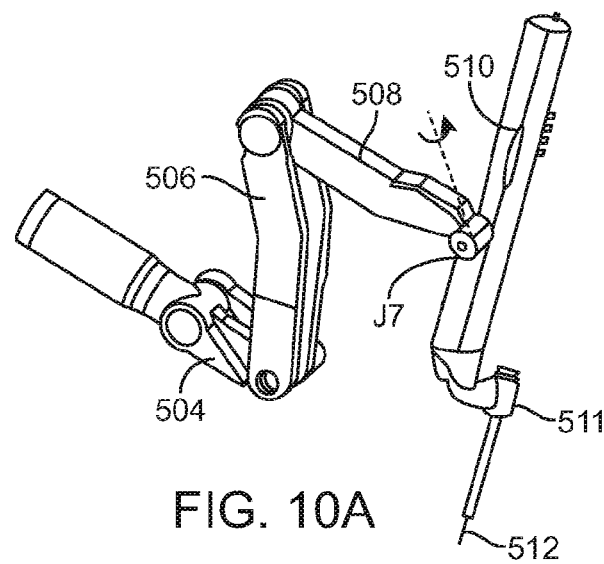
FIGS. 10A-10C show sequential views of an example manipulator arm having a revolute joint near a distal instrument holder as the joint is moved throughout its range of joint movement.
Figure 10B:
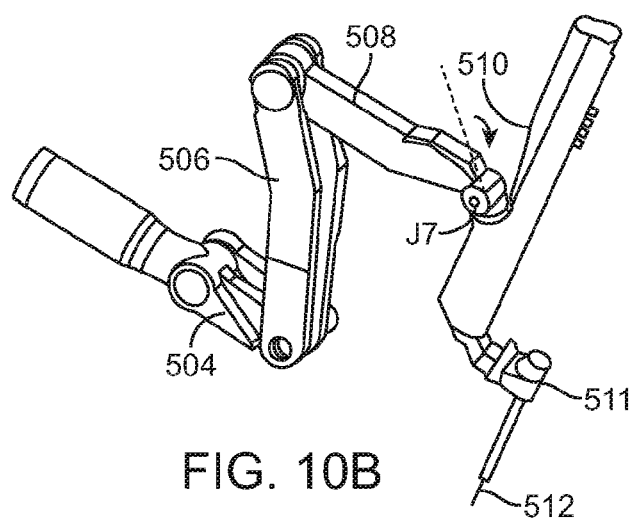
Figure 10C:
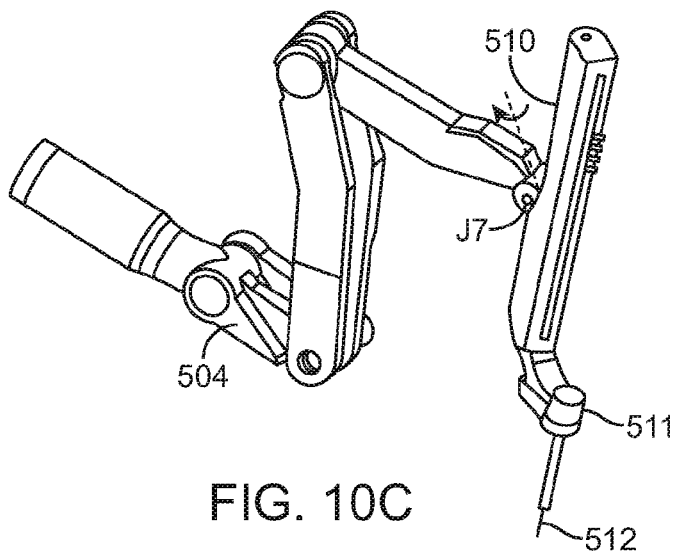

FIG. 8 illustrates another type of redundant joint for use with exemplary manipulator arms, a distal revolute joint J7 coupling the instrument holder 510 to a distal link of the manipulator arm 508. The distal revolute joint J7 allows the system to twist the instrument holder 510 about the joint axis, which in various embodiments passes through the remote center or insertion point. Ideally, the revolute joint is located distally on the arm and is therefore particularly well suited to moving the orientation of the insertion axis. The addition of this redundant axis allows the manipulator to assume multiple positions for any single instrument tip position. In general, redundant axes, such as this, allow the instrument tip to follow the surgeon's commands while simultaneously avoiding collisions with other arms or patient anatomy. Because the distal revolute joint J7 has the ability to move the insertion axis closer to the yaw axis, it is able to increase arm pitch back range of motion. The relationship between the axis of the distal revolute joint J7, the yaw axis of J1 and the insertion axis of tool tip is shown in FIG. 9. FIGS. 10A-10C show the sequential movement of the J7 and how it shifts the insertion axis of tool tip from side to side.

Figure 11A:
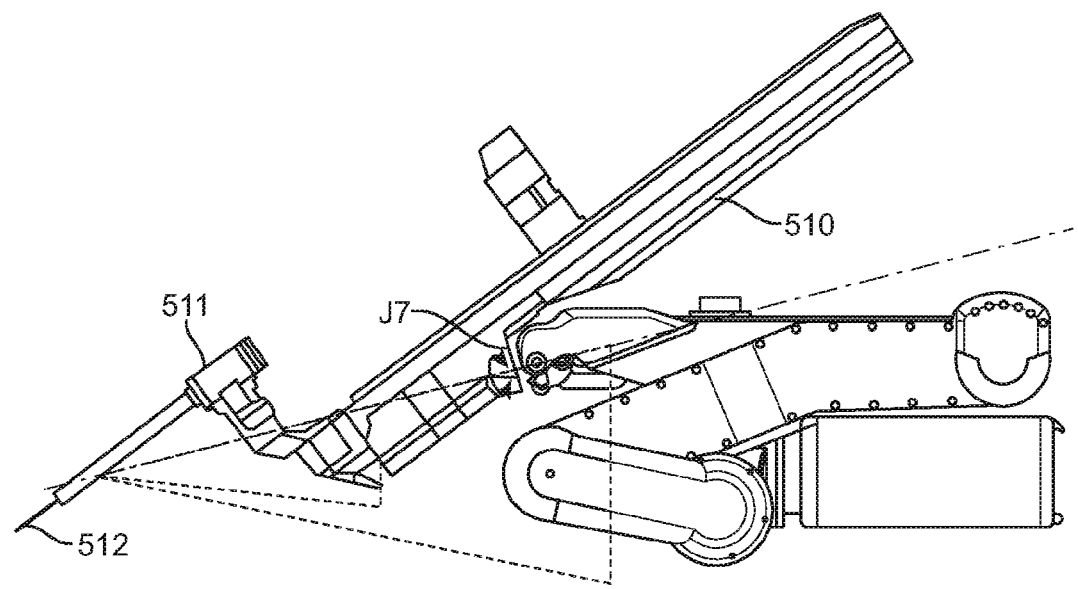
FIGS. 11A-11B show the revolved profile of an example manipulator arm having a distal revolute joint when the angular displacement of the joint is 0° versus an angular displacement of 90°, respectively.
Figure 11B:
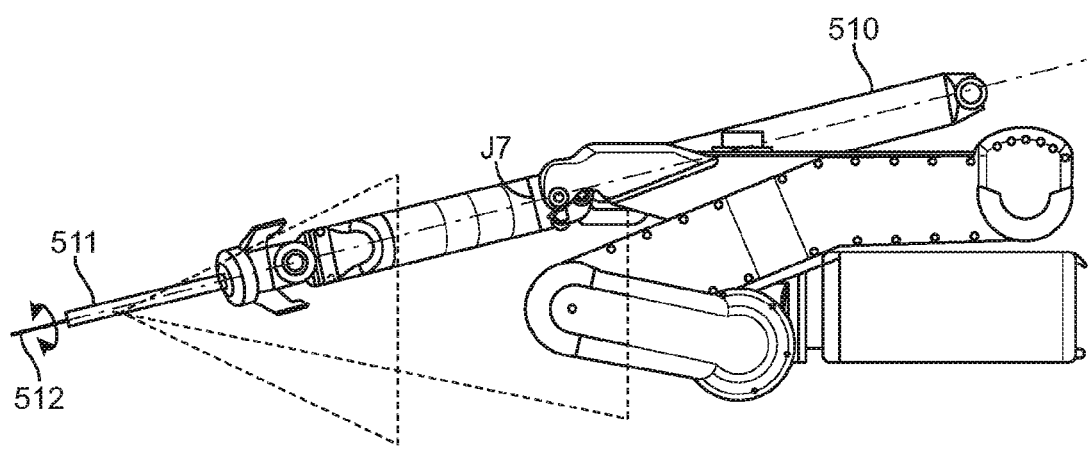
Figure 12A:
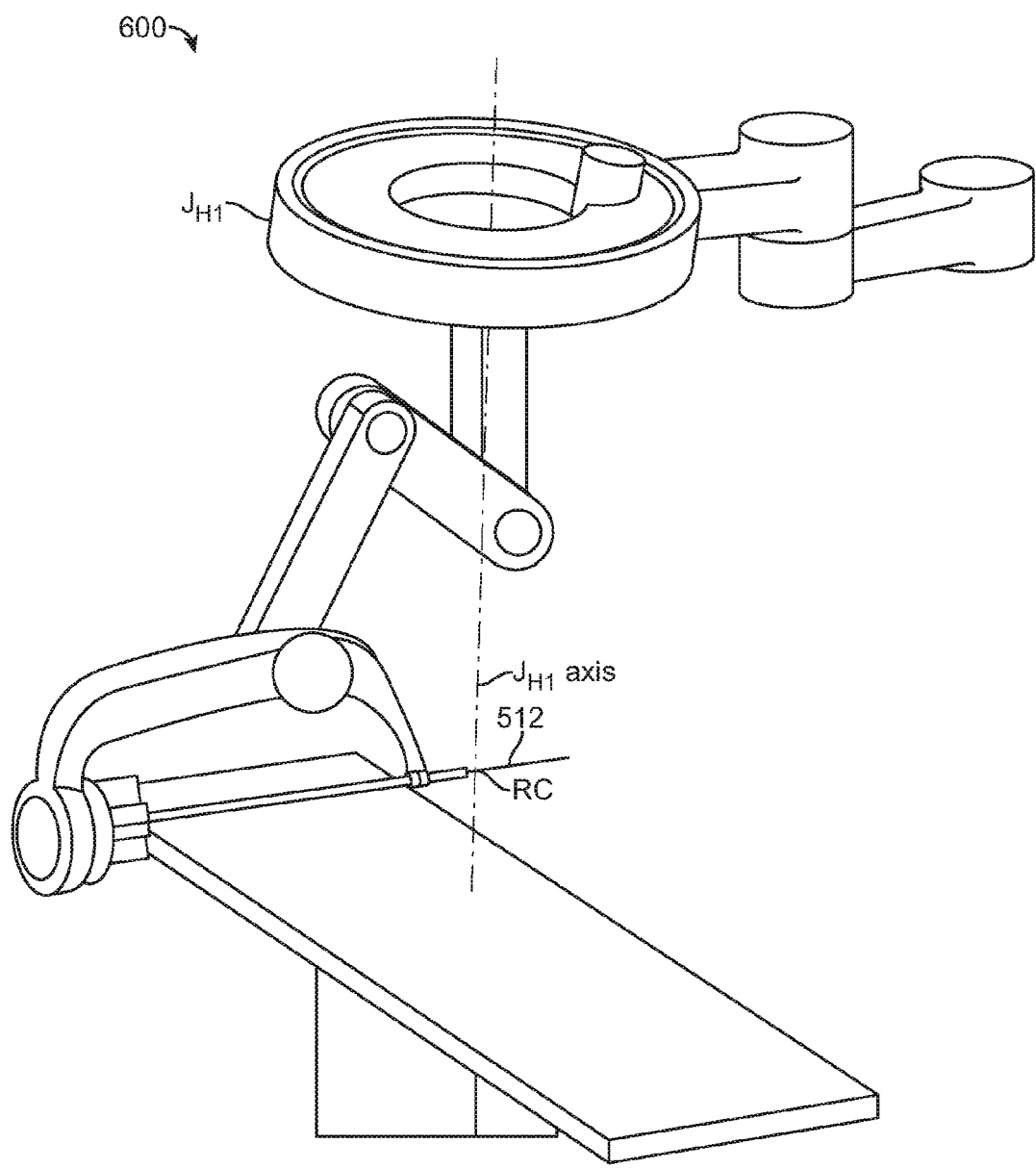
FIGS. 12A-12D show example manipulator arms having a proximal joint that translates a proximal joint supporting the manipulator arm about a path of the joint.
Figure 12B:
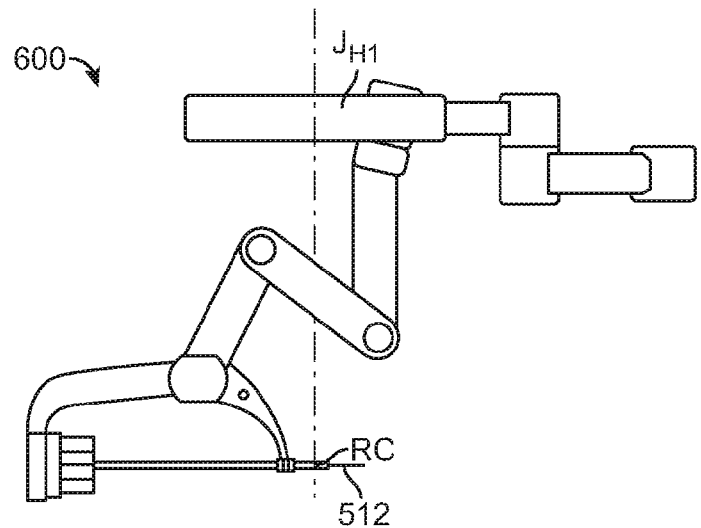
Figures 12C, 12D:
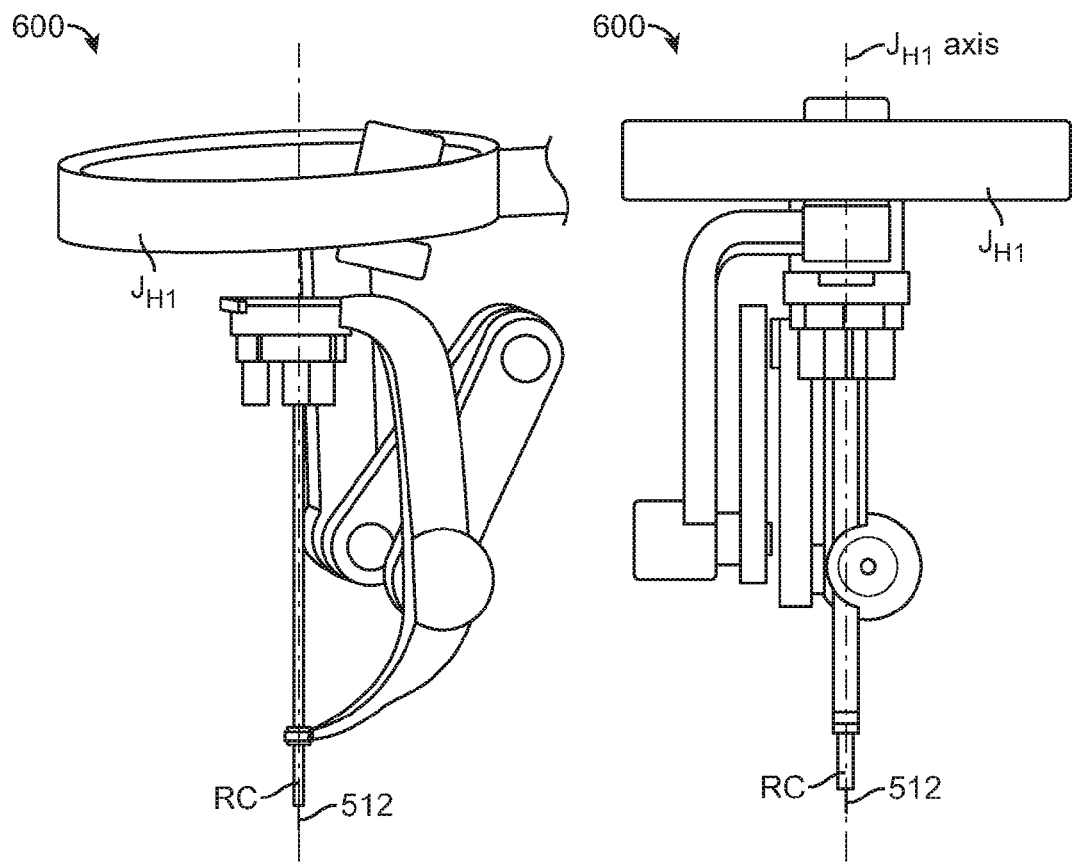

Another advantage of the distal revolute joint J7 is that it may reduce the patient clearance cone, which is the swept volume of the distal portion of the manipulator arm proximal of the insertion point that should clear the patient to avoid collision between the patient and the instrument holder or distal linkages of the manipulator arm. FIG. 11A illustrates the patient clearance cone of the proximal portion of the manipulator arm while the angular displacement of the distal revolute joint remains at 0°. FIG. 11B illustrates the reduced patient clearance cone of the proximal portion of the manipulator arm while the distal revolute joint is shown having an angular displacement of 90° about its axis. Thus, in procedures having minimal patient clearance near the insertion point, use of the joint J7 in accordance with the present invention may provide additional clearance while maintaining the remote center location or the position of the end effector as desired.

FIGS. 12A-13C illustrate another type of redundant joint for use with an exemplary manipulator arm 600, a proximal joint that translates or revolves the manipulator arm 600 about an axis. In various embodiments, this proximal translatable joint translates a proximal joint of the manipulator, such as joint J1 or $J_t$, along a path so as to reduce or eliminate the cone of silence by shifting or rotating the range of motion of the manipulator arm 600 to provide for better conditioning and improved maneuverability of the manipulator arm 600. The translatable joint may include a circular path, such as shown in joint $J_{H1}$ in FIGS. 12A-12D, or may include a semi-circular or arcuate path, such as shown in FIGS. 13A-13C. Generally, the joint revolves the manipulator arm 600 about an axis of the translatable joint that intersects with the remote center RC about which the shaft of the tool 512 extending through cannula 511 pivots. In the embodiment shown in FIGS. 12A-12D, this axis of $J_{H1}$ is a vertical axis, whereas in the embodiment shown in FIGS. 13A-13C the axis of $J_{H2}$ is horizontal.

In certain embodiments, the manipulator arm 500 may include any or all of the a proximal or distal revolute joint, a proximal translatable joint and a parallelogram configuration of the distal linkages. Use of any or all of these features provide additional redundant degrees of freedom and facilitate reconfiguration in accordance with the present invention so as to provide for a better "conditioned" manipulator assembly by increasing the angles between linkages thereby improving the dexterity and motion of the manipulator. The increased flexibility of this exemplary manipulator can also be used to optimize the kinematics of the manipulator linkage so as to avoid joint limits, singularities, and the like.

In some embodiments, the joint movements of the manipulator are controlled by driving one or more joints by a controller using motors of the system, the joints being driven according to coordinated and joint movements calculated by a processor of the controller. Mathematically, the controller may perform at least some of the calculations of the joint commands using vectors and/or matrices, some of which may have elements corresponding to configurations or velocities of the joints. The range of alternative joint configurations available to the processor may be conceptualized as a joint space. The joint space may, for example, have as many dimensions as the manipulator has degrees of freedom, and a particular configuration of the manipulator may represent a particular point in the joint space, with each coordinate corresponding to a joint state of an associated joint of the manipulator.

In an exemplary embodiment, the system includes a controller in which a commanded position and velocity of a feature in the work-space, denoted here as its Cartesian-coordinate space (referred to herein as Cartesian-space), are inputs. The feature may be any feature on the manipulator or off the manipulator which can be used as a control frame to be articulated using control inputs. An example of a feature on the manipulator, used in many examples described herein, would be the tool-tip. Another example of a feature on the manipulator would be a physical feature which is not on the tool-tip, but is a part of the manipulator, such as a pin or a painted pattern. An example of a feature off the manipulator would be a reference point in empty space which is exactly a certain distance and angle away from the tool-tip. Another example of a feature off the manipulator would be a target tissue whose position relative to the manipulator can be established. In all these cases, the end effector is associated with an imaginary control frame which is to be articulated using control inputs. However, in the following, the "end effector" and the "tool tip" are used synonymously. Although generally, there is no closed form relationship which maps a desired Cartesian space end effector position to an equivalent joint-space position, there is generally a closed form relationship between the Cartesian space end effector and joint-space velocities. The kinematic Jacobian is the matrix of partial derivatives of Cartesian space position elements of the end effector with respect to joint space position elements. In this way, the kinematic Jacobian captures the kinematic relationship between the end effector and the joints. In other words, the kinematic Jacobian captures the effect of joint motion on the end effector. The kinematic Jacobian (J) can be used to map joint-space velocities (dq/dt) to Cartesian space end effector velocities (dx/dt) using the relationship below:

$$dx/dt = J \, dq/dt$$

Thus, even when there is no closed-form mapping between input and output positions, mappings of the velocities can iteratively be used, such as in a Jacobian-based controller to implement a movement of the manipulator from a commanded user input, however a variety of implementations can be used. Although many embodiments include a Jacobian-based controller, some implementations may use a variety of controllers that may be configured to access the Jacobian of the manipulator arm to provide any of the features described herein.

One such implementation is described in simplified terms below. The commanded joint position is used to calculate the Jacobian (J). During each time step (Δt) a Cartesian space velocity (dx/dt) is calculated to perform the desired move ($dx_{des}/dt$) and to correct for built up deviation (Δx) from the desired Cartesian space position. This Cartesian space velocity is then converted into a joint-space velocity (dq/dt)

using the pseudo-inverse of the Jacobian ($J^\#$). The resulting joint-space commanded velocity is then integrated to produce joint-space commanded position (q). These relationships are listed below:

$$dx/dt = dx_{des}/dt + k\Delta x \quad (1)$$

$$dq/dt = J^\# dx/dt \quad (2)$$

$$q_i = q_{i-1} + dq/dt \Delta t \quad (3)$$

The pseudo-inverse of the Jacobian (J) directly maps the desired tool tip motion (and, in some cases, a remote center of pivotal tool motion) into the joint velocity space. If the manipulator being used has more useful joint axes than tool tip degrees of freedom (up to six), (and when a remote center of tool motion is in use, the manipulator should have an additional three joint axes for the three degrees of freedom associated with location of the remote center), then the manipulator is said to be redundant. A redundant manipulator's Jacobian includes a "null-space" having a dimension of at least one. In this context, the "null-space" of the Jacobian (N(J)) is the space of joint velocities which instantaneously achieves no tool tip motion (and when a remote center is used, no movement of the pivotal point location); and "null-motion" is the combination, trajectory or path of joint positions which also produces no instantaneous movement of the tool tip and/or location of the remote center. Incorporating or injecting the calculated null-space velocities into the control system of the manipulator to achieve the desired reconfiguration of the manipulator (including any reconfigurations described herein) changes above equation (2) to the following:

$$dq/dt = dq_{perp}/dt + dq_{null}/dt \quad (4)$$

$$dq_{perp}/dt = J^\# dx/dt \quad (5)$$

$$dq_{null}/dt = (1 - J^\# J)z = V_n V_n^T z = V_n \alpha \quad (6)$$

The joint velocity according to Equation (4) has two components: the first being the null-perpendicular-space component, the "purest" joint velocity (shortest vector length) which produces the desired tool tip motion (and when the remote center is used, the desired remote center motion) and the second being the null-space component. Equations (2) and (5) show that without a null-space component, the same equation is achieved. Equation (6) starts with a traditional form for the null-space component on the left, and on the far right side, shows the form used in an exemplary system, wherein ($V_n$) is the set of orthonormal basis vectors for the null-space, and ($\alpha$) are the coefficients for blending those basis vectors. In some embodiments, a is determined by control parameters, variables or setting, such as by use of knobs or other control means, to shape or control the motion within the null-space as desired. Utilizing above Equations (4) and (5), the following equation can be calculated to obtain null-space coefficients that can be used to drive the joints so as to cancel movement of the "locked out" joints:

$$dq/dt = dq_{perp}/dt + V_n \alpha \quad (7)$$

The joint velocity from the null-perpendicular-space generated from the pseudo-inverse of the Jacobian (see Equations (4) and (5)) is countered using the null-space velocity only for the selected joints up to the null-space dimension. If only the "non-moving" or "locked" joints are considered, the only relevant components of the vectors in Equation (7) become:

$$dq_{locked}/dt = 0 = dq_{perp(locked)}/dt + V_{n(locked)} \alpha \quad (8)$$

The relevant components of the locked out joints (Equation (8)) can then be solved according to a variety of possible solutions to obtain the null-space coefficients needed to effect joint motion cancellations. One approach is the minimum-norm, least square solution given by the pseudo-inverse denoted as $p_{inverse(\cdot)}$ in the following equation:

$$\alpha + p_{inverse}(V_{n(locked)}) dq_{perp(locked)}/dt \quad (9)$$

An alternative approach would be to use the weighted pseudo-inverse rather than the unweighted pseudo-inverse. This approach would also provide for motion cancellation of the desired joints, however in some cases, there may be drawbacks associated with this approach. For example, it may mean that no null-space algorithm is to be used or in order to use null-space basis vectors for other algorithms, both the weighted and unweighted pseudo-inverse may need to be calculated in the same kernel iteration to remain effective. Although there are other various ways in which to address these drawbacks, such methods may unnecessarily complicate the calculated movements to obtain the resulting movement allowed by the approach outlined in the equations above.

Figure 14A:
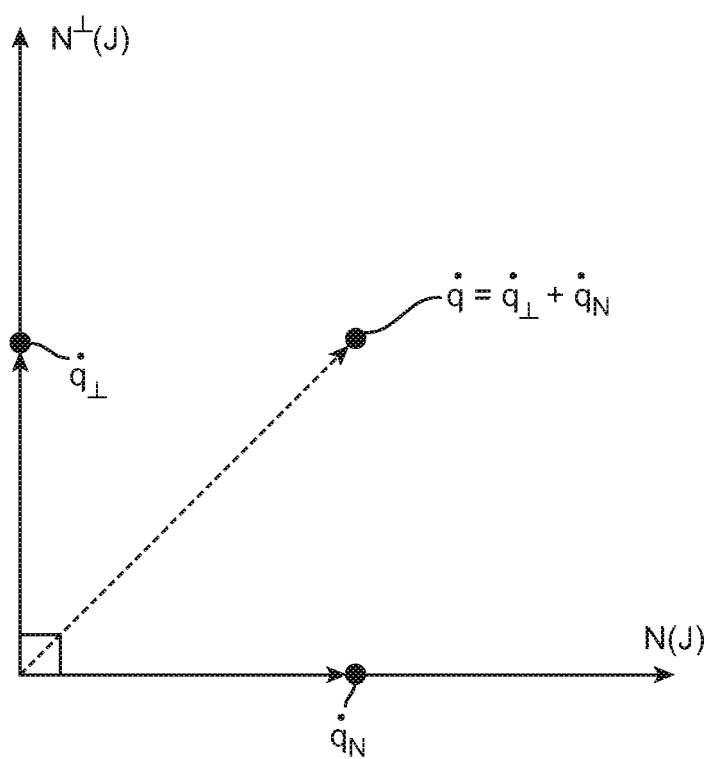
FIGS. 14A-14B graphically represent the relationship between the null-space and the null-perpendicular-space of the Jacobian of an example manipulator assembly.

FIG. 14A graphically illustrates the relationship between the null-space of the Jacobian and the null-perpendicular-space of the Jacobian of an exemplary manipulator arm. FIG. 14A shows a two-dimensional schematic showing the null-space (N(J)) along the horizontal axis, and the null-perpendicular-space ($N^\perp(J)$) along the vertical axis, the two axes being orthogonal to one another. The diagonal vector ($\dot{q}$), which represents the sum of a null-space velocity vector ($\dot{q}_N$) and a null-perpendicular-space velocity vector ($\dot{q}^\perp$), is representative of Equation (4) above.

Figure 14B:
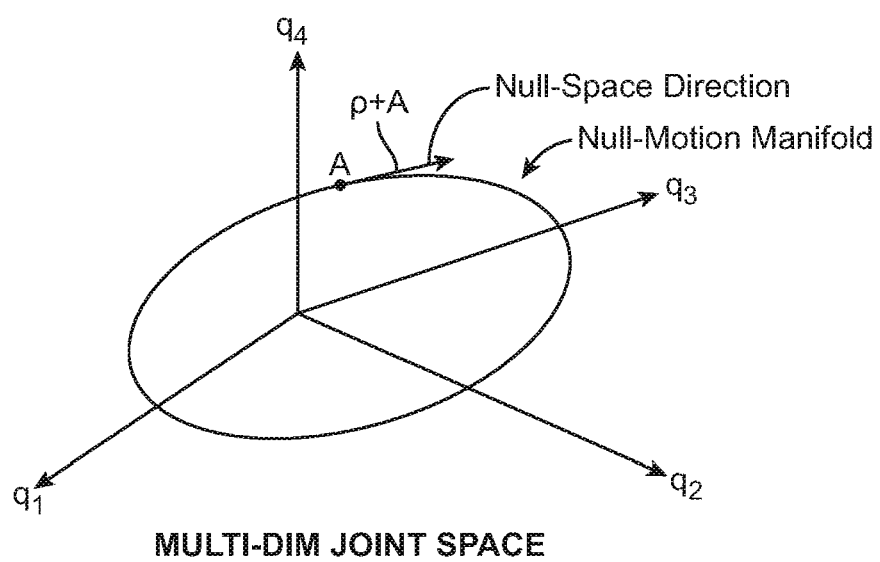

FIG. 14B graphically illustrates the relationship between the null-space and the null-motion manifold within a four-dimensional joint space, shown as the "null-motion manifold." Each arrow (q1, q2, q3, and q4) represents a principal joint axis. The closed curve represents a null-motion manifold which is a set of joint-space positions which instantaneously achieves the same end effector position. For a given point A on the curve, since the null-space is a space of joint velocities that instantaneously produce no movement of the end effector, the null-space is parallel to the tangent $\rho + A$ of the null-motion manifold at point A.

Figure 14C:
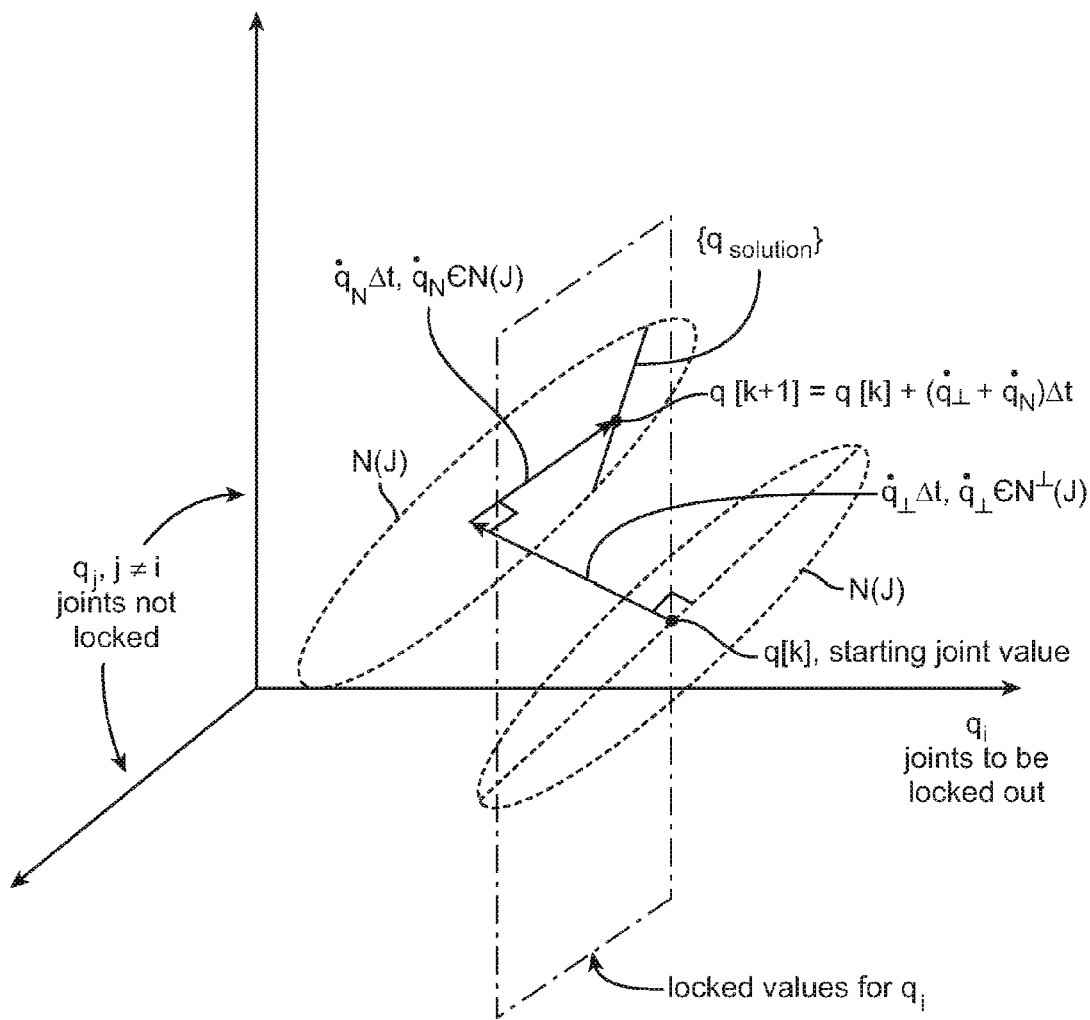
FIG. 14C graphically depicts the joint-space of the "locked" joints relative to the other joints.

FIG. 14C graphically illustrates the relationship between the "locked out" joints and the remaining joints within the joint space. The schematic shows a multi-dimensional joint-space represented by a horizontal axis representing the "non-moving" or "locked" joints ($q_i$) for which motion cancellation is provided and the vertical axis and the in/out axis representing the other joints ($q_j$) for which motion is allowed. Each axis may represent one or more joints. As described above, the motion cancellation may be applicable to certain types of movement, such as an end effector displacing movement to effect a commanded end effector manipulation, and this schematic does not address the movement of the "non-moving" or "locked out" joints that may occur in response to various other types of movement, such as a collision avoidance movement. In FIG. 14C, q[k] represents the current joint position in the multi-dimensional joints space. The diagonal arrow that points towards the upper left ($\dot{q}_\perp \in N^\perp(J)$) is the null-perpendicular vector, which is the pseudo-inverse solution to the Jacobian and is within the null-perpendicular-space. The null-perpendicular vector extends to the center of the ellipse N(J), which represents the sum of the null-perpendicular vector and the set of all null-space vectors. The dashed vertical plane ($q_i$) represents a hyperplane, which is the set of all joint configurations with the locked joints at the current q[k] value. The diagonal arrow pointing towards the upper right ($\dot{q}_N \in N(J)$) is the null-space vector. Notably, these two diagonal vectors are orthogonal to each other (the null-perpendicular space being orthogonal to the null-space). As shown, the resulting sum (tip-to-end) of these two vectors, when combined, results in a joint position having no motion along the horizontal direction that represents movement of the joints. Thus, by combining the vectors as described above, the desired joints are effectively "locked." The diagonal line $\{q_{solution}\}$ represents the intersection of the ellipse and the vertical hyperplane (the line extending within the three-dimensional joint space). Thus, $\{q_{solution}\}$ represents the set of all joint configurations that are both (i) within the null-perpendicular vector and null-space movement and (ii) that result in no movement for the joints desired to be locked. Therefore, $\{q_{solution}\}$ is the set of solution joint configurations for which the desired joints are locked out. Each of the ellipses shown in FIG. 14C corresponds to a hyperplane in joint-space represented by $\dot{q}_N \Delta t$, where $\dot{q}_N$ is a vector in the null-space within the joint velocity space. The two ellipses are separated by and perpendicular to $\dot{q}_\perp \Delta t$, while the vertical hyperplane ($q_i$) represents the joint configurations at which the locked joints are at their locked values. The point q[k] represents the joint position for time step [k], while the resulting q is represented as q[k+1], the joint position for time step [k+1], as expressed in the equation shown in FIG. 14C. In simpler terms, q[k+1] equals q[k] plus the joint movements associated with both the null-space and null-perpendicular space, q[k+1] being within the solution space denoted as $\{q_{solutions}\}$.

Figure 15A:
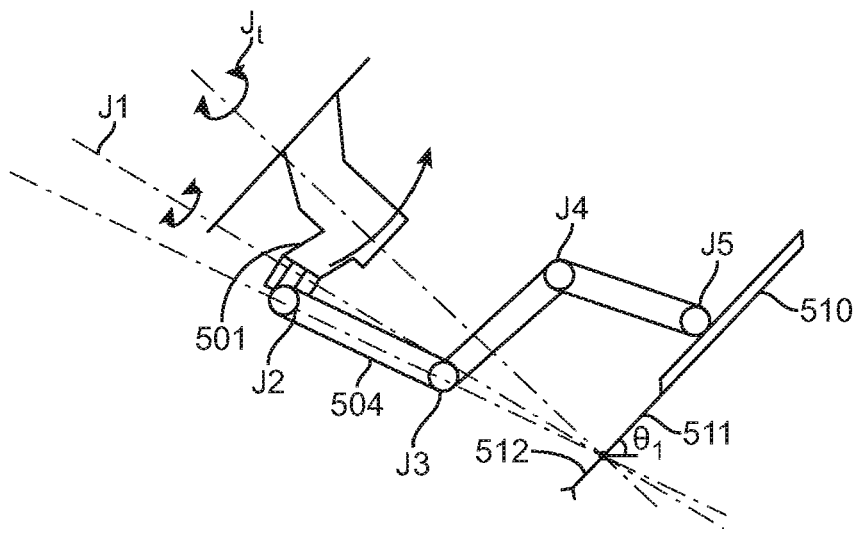
FIGS. 15A-15B illustrate movement of an example manipulator according to a reconfiguration movement concurrent with an end effector displacing movement in which the proximal-most joint is locked out of the end effector displacing movement.
Figure 15B:
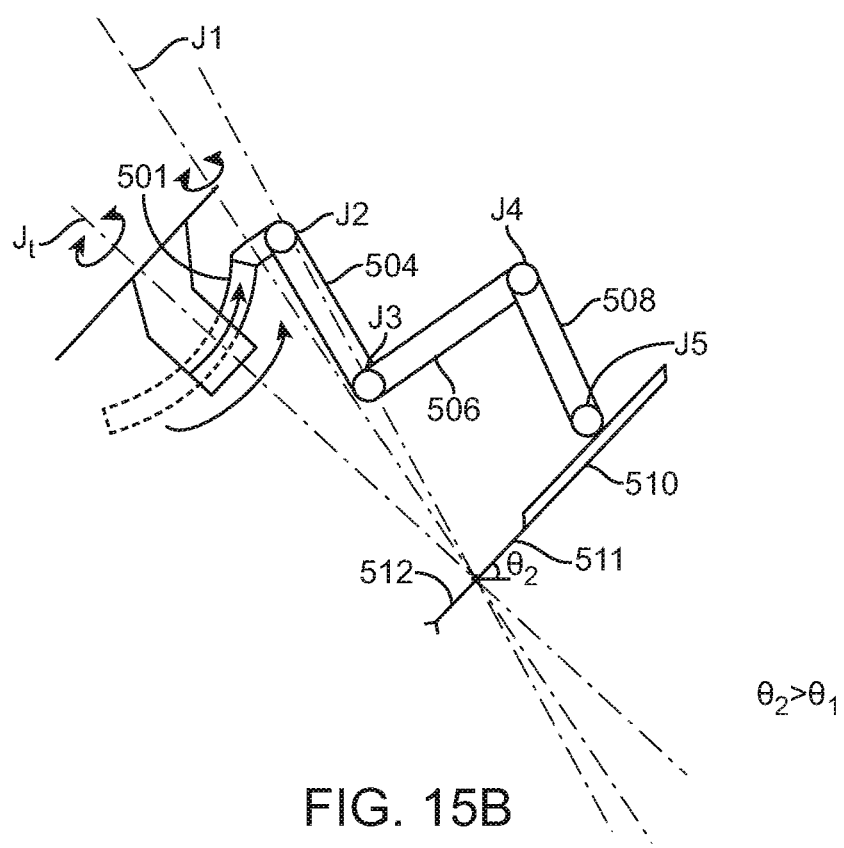

FIGS. 15A-15B schematically illustrate an example manipulator 500 before and after movement of a manipulator arm according to a reconfiguration movement concurrent with an end effector displacing movement in which joint $J_t$ is locked out. In response to an end effector manipulation command entered by a user, the processor calculates an end effector displacing movement of the joints, including joint $J_t$, within a null-perpendicular space of the Jacobian. The processor then calculates a cancellation movement of one or more joints within a null-space so that the cancellation movement of locked joint $J_t$ within the null-space cancels the joint's movement such that driving of the joints according to the calculated end effector displacing movement and cancellation movement effects the desired manipulation movement while movement of the locked joint ($J_t$) is canceled. Concurrent with the end effector displacing movement, the manipulator arm is driven according to a reconfiguration movement calculated in response to a user command to reconfigure the manipulator arm. In determining the reconfiguration movement, the movement of the joints, including locked joint $J_t$, within a null-space of the Jacobian is calculated so that the reconfiguration movement provides the desired reconfiguration of the manipulator arm while maintaining the end effector state. As shown in the example of FIG. 15A-15B, the reconfiguration movement of the arm includes movement of joint $J_t$ such that even when joint $J_t$ is locked out of the end effector displacing movement, the locked joint can move when effecting movement relating to another task, such as commanded reconfiguration of the manipulator arm.

In some embodiments, the system may be configured such that the velocities of the joints within the null-space are scaled according to the joint location and/or configuration, or any number of conditions. For example, a user may desire the proximal most joints be driven with a higher velocity than the more distal joints in the manipulator arm during reconfiguration movement. Additionally, the system may be configured so as to maintain a position or state of any one of the joints of the manipulator arm as desired.

In certain aspects, the system may receive the reconfiguration command from a system user in any number of ways. In some embodiments, the manipulator includes an input device for receiving a reconfiguration command from a user. The input device may include one or more buttons or mechanisms for driving one or more joints as desired (or alternatively for moving one or more links). The input device may be disposed on the manipulator arm, often at a location corresponding to the joint driven in response to activation of the device, such as described in U.S. Provisional Application No. 61/654,764 entitled "Commanded Reconfiguration of a Surgical Manipulator Using the Null-Space" filed Jun. 1, 2012, the entire contents of which are incorporated herein for all purposes. Alternatively, the system may include an input device having a cluster of buttons or mechanisms, each corresponding to a joint or linkage of the manipulator arm. This embodiment allows a user to reconfigure the arm from a centralized location. Alternatively, the input device may comprise a joystick that may be operated to drive one or more joints and effect reconfiguration as desired. It is appreciated that the input device may include any number of variations.

Figure 16A:
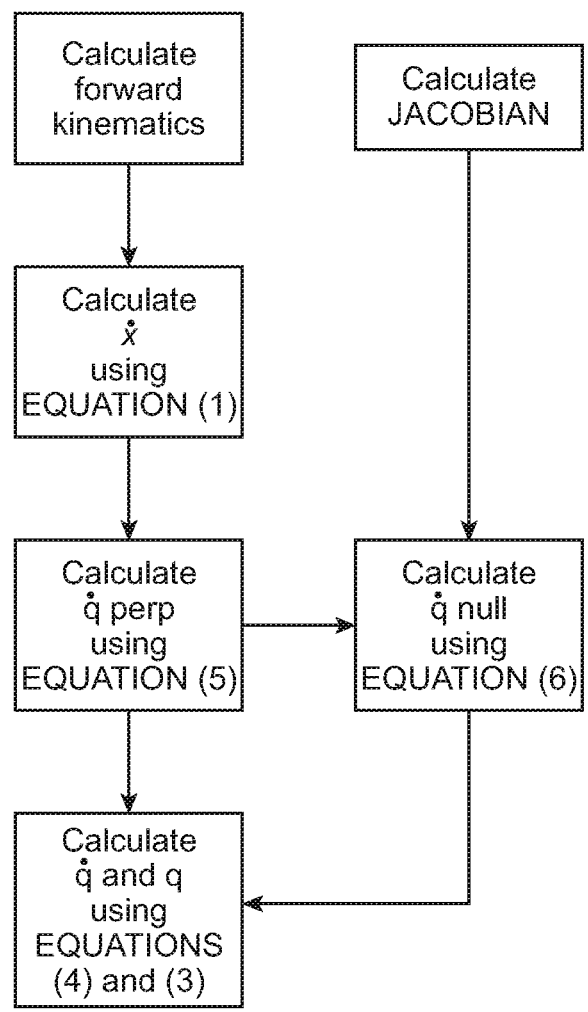
FIGS. 16A-16B are simplified block diagrams representing methods in accordance with many embodiments.
Figure 16B:
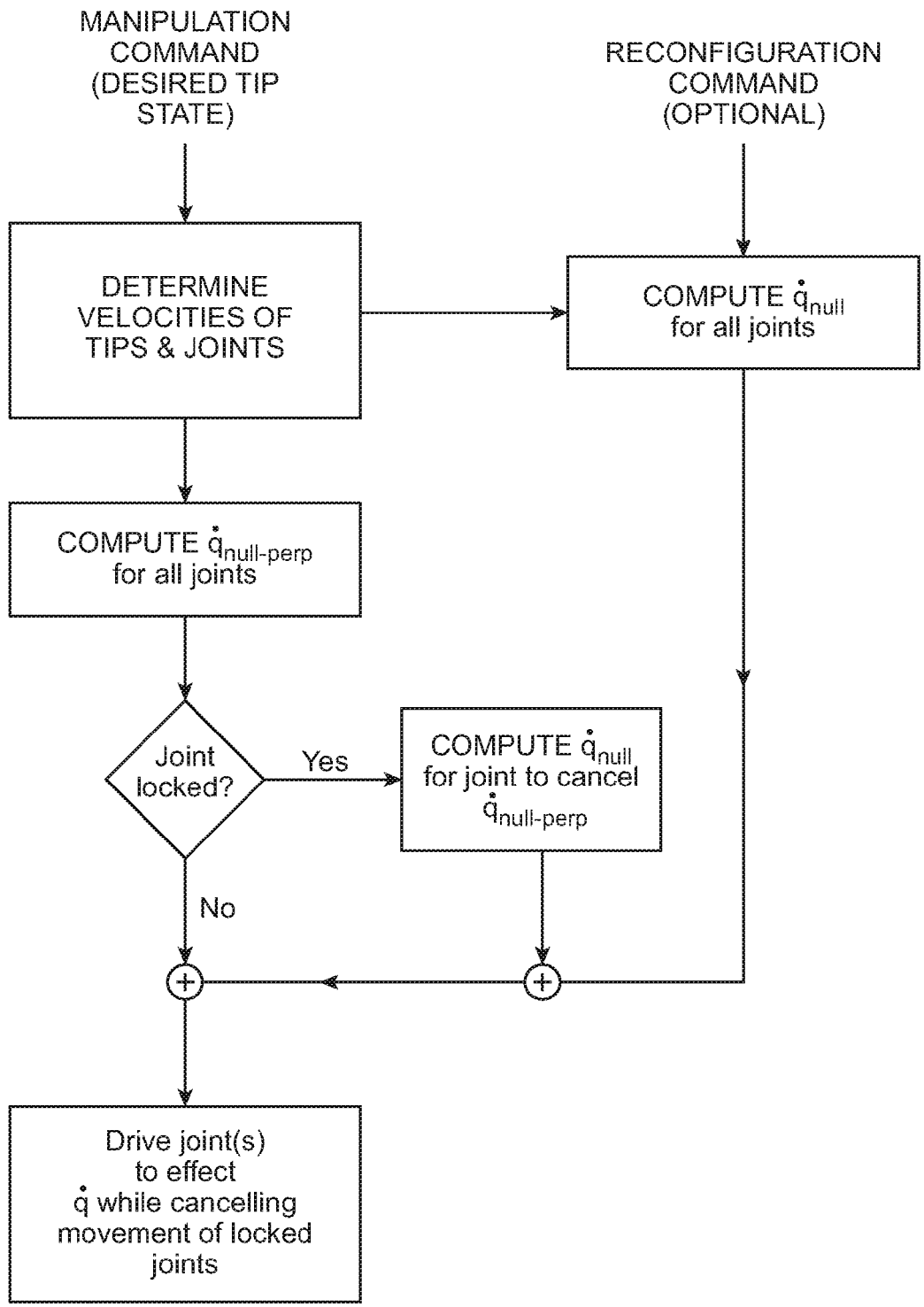

FIGS. 16A-16B illustrate methods of reconfiguring a manipulator assembly of a robotic surgical system in accordance with many embodiments of the present invention. FIG. 16A shows a simplified schematic of the required blocks need to implement the general algorithms to control the patient side cart joint states, in relation to the equations discussed above. According to the method of FIG. 16A, the system: calculates the forward kinematics of the manipulator arm; then calculates dx/dt using Equation (1), calculates $dq_{perp}/dt$ using Equation (5), then calculates $dq_{null}/dt$ from z which may depend on $dq_{perp}/dt$ and the Jacobian using Equation (6). From the calculated $dq_{perp}/dt$ and $dq_{null}/dt$ the system then calculates dq/dt and q using Equations (4) and (3), respectively, thereby providing the movement by which the controller can effect the desired reconfiguration of the manipulator while maintaining the desired state of the end effector (and/or location of the remote center).

FIG. 16B shows a block diagram of an example embodiment of the system. In response to a manipulation command, which commands a desired tool tip state, a processor of the system determines the velocities of the tool tip and the states of the joints from which the $dq_{perp}/dt$ is calculated. If any of the joints are designated as "non-moving" or "locked," the system calculates $dq_{null}/dt$ for the designated joints such that the $dq_{perp}/dt$ component and $dq_{null}/dt$ components result in no movement of the locked joints when combined. Optionally, the user may enter a reconfiguration command to reconfigure the manipulator arm if desired. In response to receiving the reconfiguration command from a user, a processor can use the determined tool tip and joint velocities (or the calculated $dq_{perp}/dt$) to calculate the $dq_{null}/dt$, after which the system adds the velocities for all joints into the calculated dq/dt so as to drive the joint(s) of the system and effect the desired movement (or state) of the end effector in which movement of the "non-moving" or "locked" joint(s) is canceled and reconfiguration of the manipulator arm, which may include movement of the locked joint(s).

While the example embodiments have been described in some detail for clarity of understanding and by way of example, a variety of adaptations, modifications, and changes will be obvious to those of skill in the art. Hence, the scope of the present invention is limited solely by the appended claims.

What is claimed is:

1. A method comprising:
receiving a command to move an end effector of a manipulator arm in an end-effector displacement, the manipulator arm including a proximal portion coupled to a base, a distal portion including the end effector, and a plurality of joints between the distal portion and the base, the plurality of joints being operable to allow a range of differing states of the plurality of joints for a given state of the distal portion;
designating one or more non-moving joints of the plurality of joints;
determining an end-effector-displacing movement of the plurality of joints to effect the end-effector displacement;
determining a cancellation movement of the plurality of joints, the cancellation movement corresponding to a non-moving end effector, and the cancellation movement providing a cancellation of joint movement for each of the one or more non-moving joints when the cancellation movement is combined with the end-effector displacing movement; and
driving the plurality of joints by combining the end-effector-displacing movement and the cancellation movement to effect the end-effector displacement.

2. The method of claim 1, wherein for each joint of the one or more non-moving joints, the corresponding joint velocities for the end-effector-displacing movement and the cancellation movement combine to effect the cancellation of joint movement for that joint.

3. The method of claim 1, further comprising:
calculating values for the cancellation movement so that, for each of the one or more non-moving joints, a corresponding joint velocity for the cancellation movement cancels a corresponding joint velocity for the end-effector-displacing movement.

4. The method of claim 1, wherein determining the end-effector-displacing movement of the plurality of joints includes calculating joint velocities of the plurality of joints from directions that correspond to a moving end effector; and
determining the cancellation movement of the plurality of joints includes calculating joint velocities of the plurality of joints from directions that correspond to a non-moving end effector.

5. The method of claim 1, further comprising:
calculating a matrix that relates joint velocities of the plurality of joints to motions of the end effector, the matrix including a plurality of joint-velocity directions corresponding to a moving end-effector and one or more joint-velocity directions corresponding to a non-moving end effector;
determining the end-effector-displacing movement of the plurality of joints from a calculation based on the plurality of joint-velocity directions corresponding to a moving end-effector; and
determining the cancellation movement of the plurality of joints from a calculation based on the one or more joint-velocity directions corresponding to a non-moving end-effector.

6. The method of claim 1, wherein determining the end-effector-displacing movement of the plurality of joints includes calculating joint velocities of the plurality of joints within a null-perpendicular space of a Jacobian matrix for the plurality of joints; and
determining the cancellation movement of the plurality of joints includes calculating joint velocities of the plurality of joints within a null space of the Jacobian, the null space being orthogonal to the null-perpendicular space.

7. The method of claim 1, further comprising:
determining an auxiliary movement of a first joint set of the plurality of joints, the first joint set being selected from the one or more non-moving joints of the plurality of joints, and the auxiliary movement being determined from directions that correspond to a non-moving end effector; and
driving the plurality of joints by combining the auxiliary movement with the end-effector-displacing movement and the cancellation movement to effect a goal of the auxiliary movement, the goal of the auxiliary movement including a desired pose, a desired configuration, or a collision avoidance for the manipulator arm.

8. A system comprising:
a manipulator arm including a proximal portion coupled to a base, a distal portion including an end effector, and a plurality of joints between the distal portion and the base, the plurality of joints being operable to allow a range of differing states of the plurality of joints for a given state of the distal portion; and
a motion unit including one or more processors configured to perform operations including:
receiving a command to move the end effector of the manipulator arm in an end-effector displacement;
designating one or more non-moving joints of the plurality of joints;
determining an end-effector-displacing movement of the plurality of joints to effect the end-effector displacement;
determining a cancellation movement of the plurality of joints, the cancellation movement corresponding to a non-moving end effector, and the cancellation movement providing a cancellation of joint movement for each of the one or more non-moving joints when the cancellation movement is combined with the end-effector displacing movement; and
driving the plurality of joints by combining the end-effector-displacing movement and the cancellation movement to effect the end-effector displacement.

9. The system of claim 8, wherein for each joint of the one or more non-moving joints, the corresponding joint velocities for the end-effector-displacing movement and the cancellation movement combine to effect the cancellation of joint movement for that joint.

10. The system of claim 8, wherein the one or more processors are further configured to perform operations including:
calculating values for the cancellation movement so that, for each of the one or more non-moving joints, a corresponding joint velocity for the cancellation movement cancels a corresponding joint velocity for the end-effector-displacing movement.

11. The system of claim 8, wherein determining the end-effector-displacing movement of the plurality of joints includes calculating joint velocities of the plurality of joints from directions that correspond to a moving end effector; and determining the cancellation movement of the plurality of joints includes calculating joint velocities of the plurality of joints from directions that correspond to a non-moving end effector.

12. The system of claim 8, wherein the one or more processors are further configured to perform operations including:
   calculating a matrix that relates joint velocities of the plurality of joints to motions of the end effector, the matrix including a plurality of joint-velocity directions corresponding to a moving end-effector and one or more joint-velocity directions corresponding to a non-moving end effector;
   determining the end-effector-displacing movement of the plurality of joints from a calculation based on the plurality of joint-velocity directions corresponding to a moving end-effector; and
   determining the cancellation movement of the plurality of joints from a calculation based on the one or more joint-velocity directions corresponding to a non-moving end-effector.

13. The system of claim 8, wherein determining the end-effector-displacing movement of the plurality of joints includes calculating joint velocities of the plurality of joints within a null-perpendicular space of a Jacobian matrix for the plurality of joints; and
   determining the cancellation movement of the plurality of joints includes calculating joint velocities of the plurality of joints within a null space of the Jacobian, the null space being orthogonal to the null-perpendicular space.

14. The system of claim 8, wherein the one or more processors are further configured to perform operations including:
   determining an auxiliary movement of a first joint set of the plurality of joints, the first joint set being selected from the one or more non-moving joints of the plurality of joints, and the auxiliary movement being determined from directions that correspond to a non-moving end effector; and
   driving the plurality of joints by combining the auxiliary movement with the end-effector-displacing movement and the cancellation movement to effect a goal of the auxiliary movement, the goal of the auxiliary movement including a desired pose, a desired configuration, or a collision avoidance for the manipulator arm.

15. A memory device including instructions that, when executed by one or more processors, cause the one or more processors to perform operations comprising:
   receiving a command to move an end effector of a manipulator arm in an end-effector displacement, the manipulator arm including a proximal portion coupled to a base, a distal portion including the end effector, and a plurality of joints between the distal portion and the base, the plurality of joints being operable to allow a range of differing states of the plurality of joints for a given state of the distal portion;
   designating one or more non-moving joints of the plurality of joints;
   determining an end-effector-displacing movement of the plurality of joints to effect the end-effector displacement;
   determining a cancellation movement of the plurality of joints, the cancellation movement corresponding to a non-moving end effector, and the cancellation movement providing a cancellation of joint movement for each of the one or more non-moving joints when the cancellation movement is combined with the end-effector displacing movement; and
   driving the plurality of joints by combining the end-effector-displacing movement and the cancellation movement to effect the end-effector displacement.

16. The memory device of claim 15, wherein for each joint of the one or more non-moving joints, the corresponding joint velocities for the end-effector-displacing movement and the cancellation movement combine to effect the cancellation of joint movement for that joint.

17. The memory device of claim 15, wherein the memory device further includes instructions that, when executed by the one or more processors, cause the one or more processors to perform operations comprising:
   calculating values for the cancellation movement so that, for each of the one or more non-moving joints, a corresponding joint velocity for the cancellation movement cancels a corresponding joint velocity for the end-effector-displacing movement.

18. The memory device of claim 15, wherein determining the end-effector-displacing movement of the plurality of joints includes calculating joint velocities of the plurality of joints from directions that correspond to a moving end effector; and
   determining the cancellation movement of the plurality of joints includes calculating joint velocities of the plurality of joints from directions that correspond to a non-moving end effector.

19. The memory device of claim 15, wherein the memory device further includes instructions that, when executed by the one or more processors, cause the one or more processors to perform operations comprising:
   calculating a matrix that relates joint velocities of the plurality of joints to motions of the end effector, the matrix including a plurality of joint-velocity directions corresponding to a moving end-effector and one or more joint-velocity directions corresponding to a non-moving end effector;
   determining the end-effector-displacing movement of the plurality of joints from a calculation based on the plurality of joint-velocity directions corresponding to a moving end-effector; and
   determining the cancellation movement of the plurality of joints from a calculation based on the one or more joint-velocity directions corresponding to a non-moving end-effector.

20. The memory device of claim 15, wherein the memory device further includes instructions that, when executed by the one or more processors, cause the one or more processors to perform operations comprising:
   determining an auxiliary movement of a first joint set of the plurality of joints, the first joint set being selected from the one or more non-moving joints of the plurality of joints, and the auxiliary movement being determined from directions that correspond to a non-moving end effector; and
   driving the plurality of joints by combining the auxiliary movement with the end-effector-displacing movement and the cancellation movement to effect a goal of the auxiliary movement, the goal of the auxiliary movement including a desired pose, a desired configuration, or a collision avoidance for the manipulator arm.

* * * * *